United States Patent [19]

Liang et al.

[11] Patent Number: 5,773,696

[45] Date of Patent: Jun. 30, 1998

[54] ANTIFUNGAL POLYPEPTIDE AND METHODS FOR CONTROLLING PLANT PATHOGENIC FUNGI

[75] Inventors: Jihong Liang; Dilip Maganlal Shah; Yonnie Shun Wu, all of Chesterfield; Cindy Annette Rosenberger, Ballwin, all of Mo.

[73] Assignee: Monsanto Company, Mo.

[21] Appl. No.: 627,706

[22] Filed: Mar. 29, 1996

[51] Int. Cl.$^6$ .............................. A01H 5/00; A01H 5/10; C12N 5/14; C12N 5/29; C12N 15/82

[52] U.S. Cl. ....................... 800/205; 435/320.1; 435/419; 435/172.3; 536/23.6; 800/255; 800/DIG. 9; 800/DIG. 15; 800/DIG. 16; 800/DIG. 17; 800/DIG. 23; 800/DIG. 26; 800/DIG. 31; 800/DIG. 38; 800/DIG. 41; 800/DIG. 42; 800/DIG. 44; 800/DIG. 46; 800/DIG. 52; 800/DIG. 55; 800/DIG. 56; 800/DIG. 57; 800/DIG. 58; 800/DIG. 63; 800/DIG. 64; 800/DIG. 67; 800/DIG. 68

[58] Field of Search ........................ 536/23.6; 435/172.3, 435/240.49, 419, 320.1; 800/200, 205, 255, DIG. 9, DIG. 15, DIG. 16, DIG. 17, DIG. 23, DIG. 26, DIG. 31, DIG. 38, DIG. 41, DIG. 42, DIG. 44, DIG. 46, DIG. 52, DIG. 55, DIG. 56, DIG. 57, DIG. 58, DIG. 63, DIG. 64, DIG. 67, DIG. 68

[56] References Cited

U.S. PATENT DOCUMENTS

| 4,940,840 | 7/1990 | Suslow et al. | 800/205 |
|---|---|---|---|
| 5,421,839 | 6/1995 | Ulbrich et al. | 47/58 |

FOREIGN PATENT DOCUMENTS

| 0 292 435 | 11/1988 | European Pat. Off. | C12N 15/00 |
|---|---|---|---|
| 0 307 841 | 3/1989 | European Pat. Off. | C12N 15/00 |
| 0 332 104 | 9/1989 | European Pat. Off. | C12N 15/00 |
| 0 385 962 | 9/1990 | European Pat. Off. | C12N 15/82 |
| 0 392 225 | 10/1990 | European Pat. Off. | C12N 15/82 |
| 0 418 695 | 3/1991 | European Pat. Off. | C12N 15/82 |
| 0 440 304 | 8/1991 | European Pat. Off. | C12N 15/56 |
| 0 448 511 | 9/1991 | European Pat. Off. | A01N 63/00 |
| 84/02913 | 8/1984 | WIPO | C07H 15/12 |
| 88/00976 | 2/1988 | WIPO | C12P 21/00 |
| 90/07001 | 6/1990 | WIPO | C12N 15/56 |
| 91/06312 | 5/1991 | WIPO | A61K 37/54 |
| 91/18984 | 12/1991 | WIPO | C12N 15/29 |
| 92/04449 | 3/1992 | WIPO | C12N 15/54 |
| 92/17591 | 10/1992 | WIPO | C12N 15/56 |
| 93/05153 | 3/1993 | WIPO | C12N 15/29 |

OTHER PUBLICATIONS

Bower and Birch, (1992) *Plant J.* 2:409.
Cuypers, et al., (1988) *Mol. Plant–Microbe Interact* 1:157–160.
Fisk, et al., (1993) *Scientia Horticulturae* 55, 5–36.
Matton, et al., (1989) *Mol. Plant–Microbe Interact.* 2:325–331.
Scoble, et al., (1993) *A Practical Guide to Protein and Peptide Purification for Microsequencing.* P. Matsudaira, Ed., Academic Press Inc., San Diego, pp. 125–153.
Smith, et al., (1981) In *Genetic Engineering: Principles and Methods*, Setlow et al., Eds., Plenum Press N.Y., pp. 1–32.
Stone and Williams, (1993) *A Practical Guide to Protein and Peptide Purification for Microsequencing.* P. Matsudaira, Ed., Academic Press Inc., San Diego, pp. 43–69.
Van Valkenburg, (1972–1973) *Pesticide Formations*, Second Edition, Mercel Dekker, N.Y.
Whitham, et al., (1994) *The Product of the Tobacco Mosaic Virus Resistance Gene N: Similarity to Toll and the Interieulin–1 Reactor,* Cell, vol. 78, 1101–1115.
Watkins, et al., (1955) *Handbook of Insecticide Dust Diluents and Carriers,* Second Edition, Dorland Books, Caldwell, H.J.
Zoller and Smith, (1982) Nucleic Acids Research, IRL Press Limited, vol. 10 No. 20.
Bowles, (1990) *Annu. Rev. Biochem,* 59:873–907.
Brears et al., (1994) *Agro–Food–Industry Hi–Tech.* 10–13.
Broekaert et al., (1995) *Plant Physiol.,* 108: 1353–1358.
Terras et al. (1992) *J. Biol. Chem.* 267:15301–15309.
Bent et al., (1994) *Science* 265:1856–1860.
Grant et al., (1995) *Cell* 78:1101–1115.
Whitham et al., (1995) *Science* 269:843–846.
Jones et al. (1994) *Science* 266:789–793.
Ellis et al., (1995) *Proc. Natl. Acad. Sci. U.S.A.* 92:4185).
Song et al., (1995) *Science* 270:1804–1806.
Van Den Ackerveken et al. (1992) *Plant J.* 2:359.
Leon et al. (1995) *Proc. Natl. Acad. Sci., USA* 92:10413–10417.
K. Masters (1979) *Spray Drying Handbook,* Third Edition, G. Goodwin, Lt., London.
Worthing and Walker (1983) *The Pesticide Manual,* Seventh Edition, British Crop Protection Council.
Boorsma et al., (1975) *J. Histochem Cytochem* 23:200–207.
Celano et al. (1993) *Bio Techniques* 15:27–28.
Sambrook et al. (1989) *Molecular Cloning: A Laboratory Manual,* Cold Spring Harbor Press, Cold Spring Harbor, N.Y.
Ausubel et al., (1995) *Current Protocols in Molecular Biology,* John Wiley & Sons, Inc.
Bauer et al. (1985) *Gene* 37–73.
Craik (1985) *Bio Techniques* 3:12–19.
Osuna et al. (1994) *Critical Reviews in Microbiology,* 20:107–116.

(List continued on next page.)

*Primary Examiner*—Douglas W. Robinson
*Assistant Examiner*—Amy J. Nelson
*Attorney, Agent, or Firm*—Arnold, White & Durkee

[57] ABSTRACT

An antifungal polypeptide, AlyAFP, that controls fungal damage to plants is provided. DNA encoding this polypeptide can be cloned into vectors for transformation of plant-colonizing microorganisms or plants, thereby providing a method of inhibiting fungal growth on plants. The polypeptide can be formulated into compositions that can be used to control undesired fungi on plants and elsewhere.

19 Claims, 12 Drawing Sheets

OTHER PUBLICATIONS

Walder et al. (1986) *Gene* 42:133.
Pyee et al. (1995) *Plant J.* 7:49–59.
Christensen et al. (1992) *Plant Mol. Biol.* 18:675–689.
Murray et al., (1989) *Nucl. Acids. Res.* 17:477–498.
T. Compton (1990) In Innis et al., Eds., *PCR Protocols, A Guide to Methods and Applications,* Academic Press, San Diego, pp. 39–45.
E. S. Kawasaki (1990) In Innis et al., Eds., *PCR Protocols, A Guide to Methods and Applications,* Academic Press, San Diego, pp. 21–27.
Mandel est al. (1995) *Plant Mol. Biol.* 29:995–1004.
Samac et al. (1991) *Plant Cell* 3:1063–1072.
McElroy et al. (1990) *Plant Cell* 2:163–171.
Bol et al. (1990) *Ann. Rev. Phytopathol.* 28:113–138.
Linthorst (1991) *Crit. Rev. Plant Sci.* 10:123–150.
Fritzemeier et al. (1987) *Plant Physiol.* 85:34–41.
Logemann et al. (1989) *Plant Cell* 1:151–158.
Schroder et al. (1992) *Plant J.* 2:161–172.
Martini et al., (1993) *Mol. Gen. Genet.* 263–179.
Weigel (1995) *Annu. Rev. Genetics* 29:19–39.
Kay et al. (1987) *Science* 236:1299.
Gordon–Kamm et al. (1990) *Plant Cell* 2:603.
Winter (1988) *Mol. Gen. Genet.* 221:315–319.
Campbell et al. (1990) *Plant Physiol.* 92:1–11.
Joaquim et al. (1991) *Phytopathology* 81:552–558.
Bytebier et al. (1987) *Proc. Natl. Acad. Sci., USA* 84:5345.
Wan and Lemaux (1994) *Plant Physiol.* 104:37.
Rhodes et al. (1988) *Science* 240:204.
Fromm et al. (1990) *Bio/Technology* 8:833.
Koziel et al. (1993) *Bio/Technology* 11:194.
Somers et al. (1992) *Bio/Technology* 10:1589.
Zhang et al. (1988) *Plant Cell Rep.* 7:379.
Luo and Wu (1988) *Plant Mol. Biol. Rep.* 6:165.
Zhang and Wu (1988) *Theor. Appl. Genet.* 76:835.
Christou et al. (1991) *Bio/Technology* 9:957.
De la Pena et al. (1987) *Nature* 325:274.
Casas et al. (1993) *Proc. Natl. Acad. Sci. USA* 90:11212.
Wang et al. (1992) *Bio/Technology* 10:691.
Zhong et al. (1993) *Plant Cell Rep.* 13:1.
Vasil et al. (1992) *Bio/Technology* 10:667.
Becker et al. (1994) *Plant J.* 5:299.
Gasser and Fraley (1989) *Science* 244:1293.
Stalker et al. (1981) *Mol. Gen. Genet* 18:8–12.
Ditta et al. (1980) *Proc. Natl. Acad. Sci. USA* 77:7347.
Murashige et al. (1962) *Physiol. Plant.* 15:473.
Fraley et al. (1983) *Proc. Natl, Acad, Acad. Sci. USA* 80:4803.

CACACNTCCCCTACACATAGATATACATACAAAATCACAGAAAGTAATAGATATGGCTAAGTTTGCTACCAT
                                                       M  A  K  F  A  T  I

CATCTCTCTTCTTGCTGCTCTTGTTCTCTTTGCTGCCTTTGAAGCACCAACAATGGTGGATGCAAGTT
 I  S  L  L  F  A  A  L  V  L  F  A  A  F  E  A  P  T  M  V  D  A  R  L
                                                                     Δ

GTGCGAGAGACCAAGTGGGACATGGTCAGGAGTTTGTGGGAACAACAATGCATGCAGGAACCAATGCAGAAA
 C  E  R  P  S  G  T  W  S  G  V  C  G  N  N  N  A  C  R  N  Q  C  R  N

CCTTGAAAGAGCAGAACACGGATCTTGCAACTATGTCTTCCCAGCTCACAAATGTATTTGTTACTTCCCATG
 L  E  R  A  E  H  G  S  C  N  Y  V  F  P  A  H  K  C  I  C  Y  F  P  C

TTAATCTACCAAATCACTTTTTGTGCTTGTGTGTATTTACATGTTATGTGTTTATTTACATGAAATAAG
 *

TCTGTGTGTCATCCCTTATGGGTGACCTTATGACACATGTACCAGATATATCATATATGTATGTTGGTTTGTTGTGT

GGCAATTATAAACTTTTTATTTGTGGATGCAAAAAAAAAAAAAAAAAAA

FIG. 1

```
AlyAFP    MAKFATIISLLFAALVLFAAFEAPTMVDA-RLCERPSGTWSGVCGNNNACRNQC
Rs-AFP1   MAKFASIIALLFAALVLFAAFEAETMVEAQKLCERPSGTWSGVCGNNNACKNQC
Rs-AFP2                               QKLCQRPSGTWSGVCGNNNACKNQC
                                      ** *                   *

AlyAFP    RNLERAEHGSCNYVFPAHKCICYFPC
Rs-AFP1   INLEKARHGSCNYVFPAHKCICYFPC
Rs-AFP2   IRLEKARHGSCNYVFPAHKCICYFPC
          ** * *
```

FIG. 2

ANTIFUNGAL POLYPEPTIDE AND METHODS FOR CONTROLLING PLANT PATHOGENIC FUNGI

FIELD OF THE INVENTION

The present invention relates to an antifungal polypeptide, AlyAFP, obtainable from flowers of plants in the genus Alyssum, and methods for controlling pathogenic fungi employing this antifungal polypeptide. The antifungal polypeptide can be applied directly to a plant, applied to a plant in the form of microorganisms that produce the polypeptide, or plants themselves can be genetically modified to produce the polypeptide. The present invention also relates to DNA sequences, microorganisms, plants, and compositions useful in these methods.

DESCRIPTION OF RELATED ART

A number of plant polypeptides and proteins exhibiting antifungal activity against a variety of plant pathogenic fungi have been isolated (Bowles (1990) Annu. Rev. Biochem. 59:873–907; Brears et al. (1994)Agro-Food-Industry Hi-Tech. 10–13). These antifungal polypeptides and proteins, encompassing several classes including chitinases, cysteine-rich chitinbinding proteins, β-1,3-glucanases, permatins (including zeamatins), thionins, ribosome-inactivating proteins, and non-specific lipid transfer proteins, are believed to play important roles in plant defense against fungal infection.

Recently, another group of plant proteins has been found to function as defensins in combatting infections by plant pathogens (PCT International Publication WO 93/05153). Two small cysteine-rich proteins isolated from radish seed, Rs-AFP1 and Rs-AFP2, were found to inhibit the growth of many pathogenic fungi when the pure protein was added to an in vitro antifungal assay medium. Transgenic tobacco plants containing the gene encoding Rs-AFP2 protein were found to be more resistant to attack by fungi than non-transformed plants.

Proteins similar to radish seed Rs-AFP2 have been isolated from seeds of many other plants (PCT International Publication WO 93/05153; Broekaert et al. (1995) Plant Physiol. 108:1353–1358). All the proteins in this group share similarity in their amino acid sequence, but differ in their antifungal activities against various fungi, especially in the presence of different mono- and divalent salts in the assay medium, which more closely resembles the physiological condition in plant cells: the antifungal activity of some antifungal proteins is dramatically reduced in the presence of 1 mM $CaCl_2$ and 50 mM KCl (Terras et al. (1992) J. Biol. Chem. 267:15301–15309). The usefulness of an antifungal protein for genetically engineering plant disease resistance can be greatly influenced by the sensitivity of the antifungal activity to salt concentration, since metal ions such as $K^+$, $Na^+$, $Ca^{2+}$, and $Mg^{2+}$ are required for normal physiological functions and are therefore abundantly present in plant cells.

The use of natural protein products to control plant pathogens has been demonstrated, for example, in European Patent Application 0 392 225.

SUMMARY OF THE INVENTION

The present inventors have discovered a new polypeptide, AlyAFP, exhibiting broad spectrum antifungal activity against plant pathogenic and other fungi. In one aspect, the present invention provides an isolated antifungal polypeptide comprising the amino acid sequence shown in SEQ ID NO:2, and biologically functional equivalents thereof.

AlyAFP, or biologically functional equivalents thereof, can be isolated from plants, or produced or synthesized by any suitable method known in the art, including direct chemical synthesis, synthesis in heterologous biological systems such as microbial, plant, and animal systems, tissue cultures, cell cultures, or in vitro translation systems.

The present invention also provides isolated DNA sequences encoding the antifungal polypeptides of the present invention, and genetic constructs and methods for inserting such DNA sequences into host cells for the production of the polypeptides encoded thereby.

The present invention also provides microorganisms and plants transformed with DNA nucleotide sequences encoding the antifungal polypeptides according to the present invention.

The present invention provides transformed plants that express antifungal polypeptides according to the invention, as well as plants that co-express these antifungal polypeptides along with other antifungal, antibacterial, or antiviral pathogenesis-related peptides, polypeptides, or proteins; insecticidal proteins, e.g., Bacillus thuringiensis (B.t.) proteins; and proteins involved in improving the quality of plant products or agronomic performance of plants. Simultaneous co-expression of multiple antifungal proteins in plants is advantageous in that it exploits more than one mode of action to control fungal damage. This can minimize the possibility of developing resistant fungal strains, broaden the scope of resistance, and potentially result in a syngergistic antifungal effect, thereby enhancing the level of resistance. Note WO 92/17591, for example, in this regard.

Examples of plants transformed to express B.t. genes are disclosed in European Patent Publication 0 385 962, which corresponds to U.S. application Ser. No. 07/476,661, filed Feb. 12, 1990, by Fischhoff et al.

Non-limiting examples of DNAs that can be co-expressed along with DNAs encoding the polypeptides of the present invention include 1) DNAs encoding enzymes such as: glucose oxidase (which converts glucose to gluconic acid, concomitantly producing hydrogen peroxide which confers broad spectrum resistance to plant pathogens); pyruvate oxidase; oxylate oxidase; cholesterol oxidase; amino acid oxidases; and other oxidases that use molecular oxygen as a primary or secondary substrate to produce peroxides, including hydrogen peroxide; 2) pathogenesis related proteins such as SAR8.2a and SARB.2b proteins; the acidic and basic forms of tobacco PR-1a, PR-1b, PR-1c, PR-1', PR-2, PR-3, PR-4, PR-5, PR-N, PR-O, PR-O', PR-P, PR-Q, PR-S, and PR-R proteins; chitinases such as tobacco basic chitinase and cucumber chitinase/lysozyme; peroxidases such as cucumber basic peroxidase; glucanases such as tobacco basic glucanase; osmotin-like proteins; 3) viral capsid proteins and replicases of plant viruses; 4) plant R-genes (resistance genes), such as Arabidopsis RPS2 (Bent et al. (1994) Science 265:1856–1860), Arabidopsis RPM1 (Grant et al. (1995) Science 269:843–846), tobacco N-gene and N'-gene (Whitham et al. (1994) Cell 78:1101–1115), tomato Cf-9 (Jones et al. (1994) Science 266:789–793), flax $L^6$ (Ellis et al. (1995) Proc. Natl. Acad. Sci. U.S.A. 92: 4185), and rice Xa21 (Song et al. (1995) Science 270: 1804–1806). These genes can be expressed using constitutive promoters, tissue-specific promoters, or promoters inducible by fungal pathogens or other biological or chemical inducers; 5) pathogen Avr genes, such as Cladosporium fulvum Avr9 (Van Den Ackerveken et al. (1992) Plant J. 2:359), that can be expressed using pathogen- or chemical-inducible promoters; and 6) genes that are involved in the biosynthesis of salicylic acid, such as benzoic acid 2-hydroxylase (Leon et al. (1995) *Proc. Natl. Acad. Sci. USA* 92:10413–10417).

A number of publications have discussed the use of plant and bacterial glucanases, chitinases, and lysozymes to produce transgenic plants exhibiting increased resistance to various microorganisms such as fungi. These include EP 0 292 435, EP 0 290 123, WO 88/00976, U.S. Pat. No. 4,940,840, WO 90/07001, EP 0 392 225, EP 0 307 841, EP 0 332 104, EP 0 440 304, EP 0 418 695, EP 0 448 511, and WO 91/06312. The use of osmotin-like proteins is discussed in WO 91/18984.

In accomplishing the foregoing, there is provided in accordance with various aspects of the present invention:

An isolated polypeptide comprising the amino acid sequence shown in SEQ ID NO:2.

An isolated DNA molecule encoding this isolated polypeptide. The isolated DNA molecule can be a cDNA molecule comprising the nucleotide sequence shown in SEQ ID NO:12. Alternatively, this cDNA molecule can comprise nucleotides 116 to 269 of the nucleotide sequence shown in SEQ ID NO:12.

A recombinant, double-stranded DNA molecule, comprising operatively linked in the 5' to 3' direction:
a) a promoter that functions in plant cells to cause the production of an RNA sequence;
b) a structural coding sequence that encodes a polypeptide comprising the amino acid sequence shown in SEQ ID NO:2; and
c) a 3' non-translated region that functions in plant cells to cause transcriptional termination and the addition of polyadenylate nucleotides to the 3' end of said RNA sequence.

The structural coding sequence of the foregoing DNA molecule can be a cDNA molecule comprising the nucleotide sequence shown in SEQ ID NO:12, or nucleotides 116 to 269 of the nucleotide sequence shown in SEQ ID NO:12. Similar recombinant, double-stranded DNA molecules, containing appropriate promoters and other regulatory sequences, can be introduced into animal, fungal, and bacterial cells to obtain transformed cells expressing the structural coding sequence.

The promoter of the foregoing DNA molecule can be the FMV 35S promoter, the CaMV 35S promoter, the ssRUBISCO promoter, the eIF-4A promoter, the LTP promoter, the actin promoter, or the ubiquitin promoter.

A method of controlling fungal damage to a plant, comprising providing to the locus of said plant an isolated polypeptide comprising or consisting essentially of the amino acid sequence shown in SEQ ID NO:2. The fungal damage can be caused by a fungus selected from the group consisting of the genera Alternaria; Ascochyta; Botrytis; Cercospora; Colletotrichum; Diplodia; Erysiphe; Fusarium; Gaeumanomyces; Helminthosporium; Macrophomina; Nectria; Peronospora; Phoma; Phymatotrichum; Phytophthora; Plasmopara; Podosphaera; Puccinia; Puthium; Pyrenophora; Pyricularia; Pythium; Rhizoctonia; Scerotium; Sclerotinia; Septoria; Thielaviopsis; Uncinula;Venturia; and Verticillium. In this method, the polypeptide can be provided to the plant locus by plant-colonizing microorganisms which produce the antifungal polypeptide, by applying a composition comprising the isolated polypeptide thereto, or by expressing DNA encoding the polypeptide within cells of the plant.

A method of controlling fungal damage to a plant, comprising the steps of:

a) inserting into the genome of a plant cell a recombinant, double-stranded DNA molecule comprising:
(i) a promoter that functions in plant cells to cause the production of an RNA sequence;
(ii) a structural coding sequence that encodes a polypeptide comprising the amino acid sequence shown in SEQ ID NO:2;
(iii) a 3' non-translated region that functions in said plant cells to cause transcriptional termination and the addition of polyadenylate nucleotides to the 3' end of said RNA sequence;
b) obtaining transformed plant cells; and
c) regenerating from said transformed plant cells a genetically transformed plant, cells of which express an antifungal effective amount of said polypeptide.

In the foregoing method, the structural coding sequence can comprise the nucleotide sequence shown in SEQ ID NO:12, or nucleotides 116 to 269 of the nucleotide sequence shown in SEQ ID NO:12. The promoter can be the FMV 35S promoter, the CaMV 35S promoter, the ssRUBISCO promoter, the EIF-4A promoter, the LTP promoter, the actin promoter, or the ubiquitin promoter.

A plant, cells of which contain an antifungal effective amount of a polypeptide comprising the amino acid sequence shown in SEQ ID NO:2.

The foregoing plant can be produced by a method comprising the steps of:

a) inserting into the genome of a plant cell a recombinant, doublestranded DNA molecule comprising:
(i) a promoter that functions in plant cells to cause the production of an RNA sequence;
(ii) a structural coding sequence that encodes a polypeptide comprising the amino acid sequence shown in SEQ ID NO:2;
(iii) a 3' non-translated region that functions in said plant cells to cause transcriptional termination and the addition of polyadenylate nucleotides to the 3' end of said RNA sequence;
b) obtaining transformed plant cells; and
c) regenerating from said transformed plant cells a genetically transformed plant, cells of which expresses an antifungal effective amount of said polypeptide.

The structural coding sequence employed in the foregoing method can comprise the nucleotide sequence shown in SEQ ID NO:12, or nucleotides 116 to 269 of the nucleotide sequence shown in SEQ ID NO:12.

Furthermore, the genome of this plant can comprise one or more additional DNA molecules encoding an antifungal peptide, polypeptide, or protein, wherein said one or more additional DNA molecules are expressed and produce an antifungal effective amount of said peptide, polypeptide, or protein encoded thereby. The additional DNA molecule can also comprise DNA encoding a *B.t.* endotoxin, wherein said DNA is expressed and produces an anti-insect effective amount of *B.t.* endotoxin. This plant can be a member selected from the group consisting of apple, barley, broccoli, cabbage, canola, carrot, citrus, corn, cotton, garlic, oat, onion, an ornamental plant, pea, peanut, pepper, potato, rice, rye, sorghum, soybean, strawberry, sugarbeet, sugarcane, tomato, a vine, and wheat. The present invention also encompasses a potato seedpiece produced by this plant.

A method of combatting an undesired fungus, comprising contacting the undesired fungus with an antifungal effective amount of an isolated polypeptide comprising the amino acid sequence shown in SEQ ID NO:2.

An antifungal composition, comprising an antifungal effective amount of an isolated polypeptide comprising the amino acid sequence shown in SEQ ID NO:2, and an acceptable carrier. The antifungal composition can be used for inhibiting the growth of, or killing, pathogenic fungi. These compositions can be formulated by conventional methods such as those described in, for example, Winnacker-Kuchler (1986) *Chemical Technology*, Fourth Edition, Volume 7, Hanser Verlag, Munich; van Falkenberg (1972–1973) *Pesticide Formulations*, Second Edition, Marcel Dekker, N.Y.; and K. Martens (1979) *Spray Drying Handbook*, Third Edition, G. Goodwin, Ltd., London. Necessary formulation aids, such as carriers, inert materials, surfactants, solvents, and other additives are also well known in the art, and are described, for example, in Watkins, *Handbook of Insecticide Dust Diluents and Carriers*, Second Edition, Darland Books, Caldwell, N.J., and Winnacker-Kuchler (1986) *Chemical Technology*, Fourth Edition, Volume 7, Hanser Verlag, Munich. Using these formulations, it is also possible to prepare mixtures of the present antifungal polypeptide with other pesticidally active substances, fertilizers and/or growth regulators, etc., in the form of finished formulations or tank mixes.

Antifungal compositions contemplated herein also include those in the form of host cells, such as bacterial and fungal cells, capable of the producing the present antifungal polypeptide, and which can colonize roots and/or leaves of plants. Examples of bacterial cells that can be used in this manner include strains of Agrobacterium, Arthrobacter, Azospyrillum, Clavibacter, Escherichia, Pseudomonas, Rhizobacterium, and the like.

Numerous conventional fungal antibiotics and chemical fungicides with which the present antifungal polypeptide can be combined are known in the art and are described in Worthington and Walker (1983) *The Pesticide Manual*, Seventh Edition, British Crop Protection Council. These include, for example, polyoxines, nikkomycines, carboxyamides, aromatic carbohydrates, carboxines, morpholines, inhibitors of sterol biosynthesis, and organophosphorus compounds. Other active ingredients which can be formulated in combination with the present antifungal polypeptide include, for example, insecticides, attractants, sterilizing agents, acaricides, nematocides, and herbicides. U.S. Pat. No. 5,421,839 contains a comprehensive summary of the many active agents with which substances such as the present antifungal polypeptide can be formulated.

Whether alone or in combination with other active agents, the antifungal polypeptide of the present invention should be applied at a concentration in the range of from about 0.1 $\mu$g/ml to about 100 mg/ml, preferably between about 5 $\mu$g/ml and about 5 mg/ml, at a pH in the range of from about 3.0 to about 9.0. Such compositions can be buffered using, for example, phosphate buffers between about 1 mM and 1M, preferably between about 10 mM and 100 mM, more preferably between about 15 mM and 50 mM. In the case of low buffer concentrations, it is desirable to add a salt to increase the ionic strength, preferably NaCl in the range of from about 1 mM to about 1M, more preferably about 10 mM to about 100 mM.

Further scope of the applicability of the present invention will become apparent from the detailed description and drawings provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

BRIEF DESCRIPTIONS OF THE DRAWINGS

The above and other objects, features, and advantages of the present invention will be better understood from the following detailed description taken in conjunction with the accompanying drawings, all of which are given by way of illustration only and are not limitative of the present invention.

DNA fragments common to the plasmid maps presented herein are: AMP: ampicillin resistance; ori-pUC: replication origin derived from pUC plasmid; LAC: partial sequence of the Lac Z gene; p-e35S: promoter e35S; HSP70 intron: the intron of heat shock protein 70 from maize; NOS3': 3' untranslated region of the nopaline synthase (nos) gene of Agrobacterium Ti plasmid; ori-M13: M13 phage replication origin; Spc/Str: bacterial spectinomycin/streptomycin resistance gene; p-FMV: figwort mosaic virus 35S promoter; EPSPS/CTP2: chloroplast transit peptide from the rabidopsis 5-enopyruvyl-3-phosphoshikimate synthase gene (EPSPS); CP4 syn: synthetic bacterial glyphosate resistance CP4 5-enolpyruvyl-3-phosphoshikimate synthase (EPSPS) gene; E9 3': 3' untranslated region of he pea ssRUBISCO E9 gene; PetHSP70-Leader: 5' untranslated leader sequence of petunia heat shock protein 70 gene; ori-322: pUC322 replication origin.

FIG. 1 shows the cDNA nucleotide sequence and deduced amino acid sequence of AlyAFP. The triangle indicates the start of the mature AlyAFP polypeptide. The underlined amino acid sequence indicates the signal peptide. The double underlined sequence indicates a potential polyA signal sequence. The asterisk denotes the stop codon.

FIG. 2 is a pileup comparison of the amino acid sequences of AlyAFP, Rs-AFP1, and Rs-AFP2. The triangle indicates the start of the mature AlyAFP and Rs-AFP1 polypeptides. The underlined amino acid sequences indicate signal peptides (the signal peptide sequence for Rs-AFP2 has not been determined), and the asterisks indicate differences among the three peptides.

DETAILED DESCRIPTION OF THE INVENTION

Figure 3:
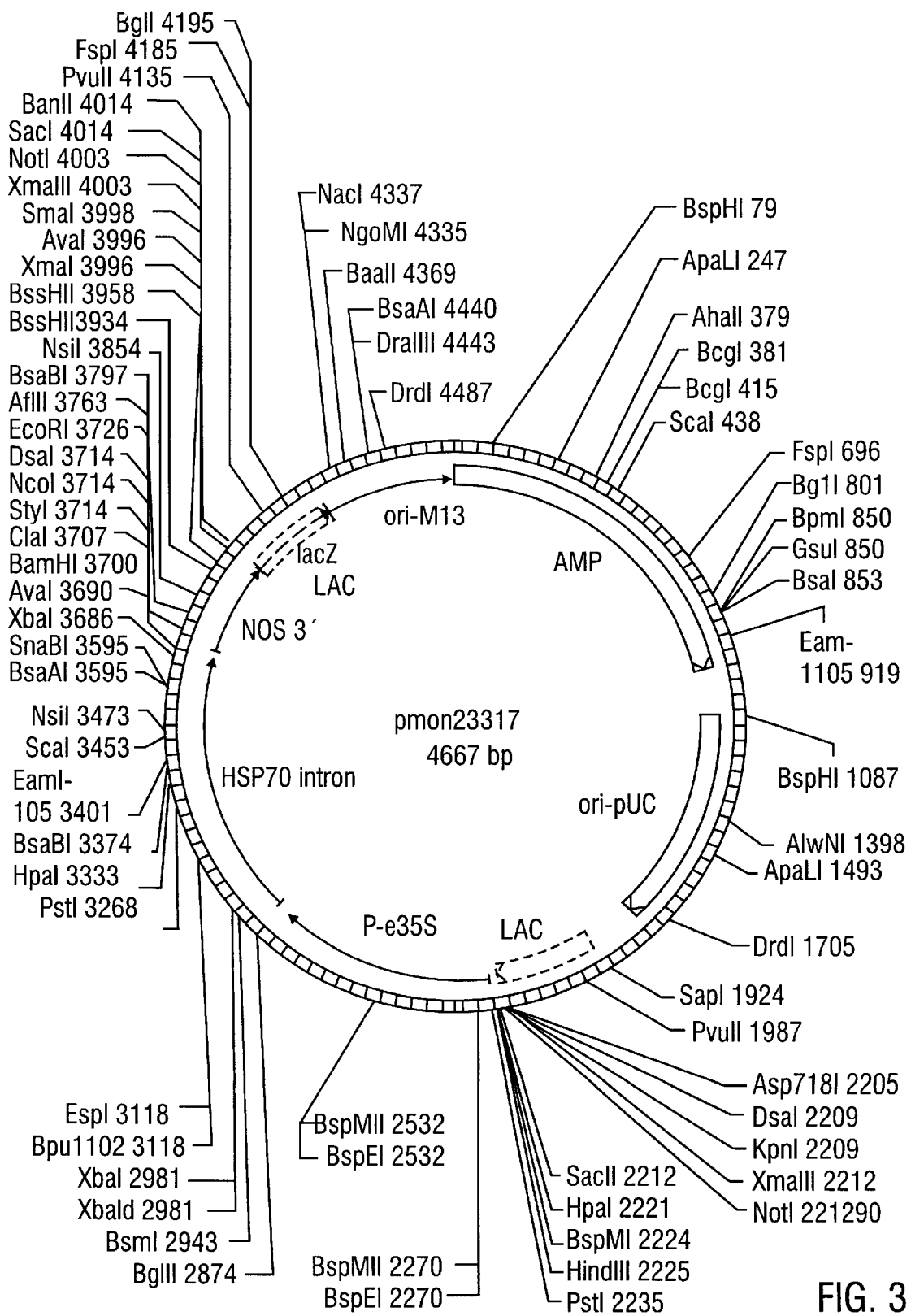
FIG. 3 is a physical map of pMON23317.

The following detailed description of the invention is provided to aid those skilled in the art in practicing the present invention. Even so, the following detailed description should not be construed to unduly limit the present invention as modifications and variations in the embodiments discussed herein may be made by those of ordinary skill in the art without departing from the spirit or scope of the present inventive discovery.

The contents of each of the references discussed in this specification, including the references cited therein, are herein incorporated by reference in their entirety.

Definitions

As used herein, the term "antifungal polypeptide" refers to a polypeptide having antifungal properties, e.g., which inhibits the growth of fungal cells, or which kills fungal cells, or which disrupts or retards stages of the fungal life cycle such as spore germination, sporulation, and mating.

The phrase "combatting or controlling fungal damage" in an agricultural context refers to reduction in damage to a crop due to infection by a fungal pathogen. More generally, this phrase refers to reduction in the adverse effects caused by the presence of an undesired fungus in any particular locus.

The term "structural coding sequence" refers to a DNA sequence that encodes a peptide, polypeptide, or protein that is made by a cell following transcription of the structural coding sequence to messenger RNA (mRNA), followed by translation of the mRNA to the desired peptide, polypeptide, or protein product.

The method of the present invention can be carried out in a variety of ways. The present antifungal polypeptides, prepared by any of the methods noted above, can be applied directly to plants in a mixture with carriers or other additives, including other antifungal agents, as is known in the art. Alternatively, the polypeptides can be expressed by bacterial or yeast cells that can be applied to the plant. Plant cells can also be transformed by conventional means to contain DNA encoding the antifungal polypeptides. These can be expressed constitutively, in a tissuespecific manner, or upon exposure of the plant to a fungal pathogen.

In a particular aspect, the present invention comprises the use of a polypeptide having the sequence shown in SEQ ID NO:2, which exhibits strong antifungal activity against a variety of different plant pathogenic fungi.

The amino acid sequence of this antifungal polypeptide has been determined by direct sequencing and by translation of the cloned cDNA therefor. Although it is partially homologous, i.e., possesses partial sequence identity, to other plant defensins, this antifungal polypeptide differs from each and every other plant defensin in more than 10% of its amino acid residues. In addition, the antifungal activity of this polypeptide is significantly greater than that of the most closely related plant defensins (Rs-AFP1 and Rs-AFP2), especially when assayed in the presence of inorganic cations at physiological concentrations. A pile-up diagram comparing the amino acid sequence of AlyAFP with that of Rs-AFP1 and Rs-AFP2 is shown in FIG. 2.

The present invention also encompasses the use of any of the DNA sequences or biologically functional equivalents thereof disclosed herein to produce recombinant plasmids, transformed microorganisms, probes, and primers useful in identifying related DNA sequences that confer resistance to fungal pathogens on plant cells, and to produce transgenic plants resistant to such fungal pathogens.

The present invention also encompasses methods of conferring resistance to fungal pathogens on plant cells and plants by using the DNA sequences or biologically functional equivalents thereof disclosed herein.

As noted above, the antifungal polypeptides of the present invention can be used in combination with other antifungal agents, including other peptides, polypeptides, and proteins that exhibit antifungal activity, so as to provide a broad spectrum of activity, i.e., to control additional pathogens, and/or to provide multiple modes of action for the control of the same fungal pathogen. Examples of such other antifungal agents include chitinases, cysteine-rich chitin-binding proteins, β-1,3-glucanases, permatins (including zeamatins), thionins, ribosome-inactivating proteins, and non-specific lipid transfer proteins.

Sources of such antifungal polypeptides and proteins include plants such as Arabidopsis, barley, broccoli, cabbage, canola, carrot, corn, garlic, onion, pea, pepper, potato, rice, soybean, sugarbeet, tobacco, tomato, and wheat; microorganisms such as Aspergillus, Penicilium, Streptomyces, Alternaria (*Alternaria brassicola; Alternaria solani*); Ascochyta (*Ascochyta pisi*); Botrytis (*Botrytis cinerea*); Cercospora (*Cercospora kikuchii; Cercospora zaea-maydis*); Colletotrichum (*Colletotrichum lindemuthianum*); Diplodia (*Diplodia maydis*); Erysiphe (*Erysiphe graminis f.sp. graminis; Erysiphe graminis f.sp. hordei*); Fusarium (*Fusarium nivale; Fusarium oxysporum; Fusarium graminearum; Fusarium culmorum; Fusarium solani; Fusarium moniliforme; Fusarium roseum*); Gaeumanomyces (*Gaeumanomyces graminis f.sp. tritici*); Helminthosporium (*Helminthosporium turcicum; Helminthosporium carbonum; Helminthosporium maydis*); Macrophomina (*Macrophomina phaseolina; Maganaporthe grisea*); Nectria (*Nectria heamatococca*); Peronospora (*Peronospora manshurica; Peronospora tabacina*); Phoma (*Phoma betae*); Phymatotrichum (*Phymatotrichum omnivorum*); Phytophthora (*Phytophthora cinnamomi; Phytophthora cactorum; Phytophthora phaseoli; Phytophthora parasitica; Phytophthora citrophthora; Phytophthora megasperma f.sp. sojae; Phytophthora infestans*); Plasmopara (*Plasmopara viticola*); Podosphaera (*Podosphaera leucotricha*); Puccinia (*Puccinia sorghi; Puccinia striiformis; Puccinia graminis f.sp. tritici; Puccinia asparagi; Puccinia recondita; Puccinia arachidis*); Puthium (*Puthium aphanidermatum*); Pyrenophora (*Pyrenophora triticirepentens*); Pyricularia (*Pyricularia oryzae*); Pythium (*Pythium ultimum*); Rhizoctonia (*Rhizoctonia solani; Rhizoctonia cerealis*); Scerotium (*Scerotium rolfsii*); Sclerotinia (*Sclerotinia sclerotiorum*); Septoria (*Septoria lycopersici; Septoria glycines; Septoria nodorum; Septoria tritici*); Thielaviopsis (*Thielaviopsis basicola*); Uncinula (*Uncinula necator*); Venturia (*Venturia inaequalis*); and Verticillium (*Verticillium dahliae; Verticillium albo-atrum*); and other nonplant organisms.

The present invention can be better understood from the following illustrative, non-limiting Examples.

EXAMPLE 1

Molecular Weight of AlyAfp

Gel Electrophoresis

The molecular weight of AlyAFP was initially determined electrophoretically by the method of Laemmli ((1970) *Nature* 227:680–685). The polypeptide was dissolved in denaturing sample buffer containing 450 mM Tris-HCl, pH 8.45, 12% glycerol, 4% SDS, 0.06% Coomassie Blue G, and 0.0025% Phenol Red (Novex, San Diego, Calif.), boiled for 10 min., and electrophoresed in a 16% Tricine gel (Novex, San Diego, Calif.) in electrophoresis buffer containing 100 mM Tris, 100 mM Tricine, and 1% SDS at 125 V constant voltage for two hours. Silver staining (Integrated Separation Systems, Natick, Mass.) revealed a band having a molecular weight of approximately 6 kDa.

Mass Analysis by Positive Ion Electrospray Mass Spectrometry

AlyAFP was mass-analyzed by positive ion electrospray mass spectrometry as described by Scoble et al. ((1993) in *A Practical Guide to Protein and Peptide Purification for Microsequencing*, P. Matsudaira, Ed., Academic Press, Inc., San Diego, pp. 125–153).

The observed molecular weight of the native polypeptide was 5,657 daltons.

Analysis of tryptic Fragments

The antifungal polypeptide was reduced, carboxymethylated, and digested with trypsin by the method of Stone and Williams ((1993) *A Practical Guide to Protein and Peptide Purification for Microsequencing*, P. Matsudaira, Ed., Academic Press, Inc., San Diego, pp.43–69).

The tryptic digests were analyzed by capillary liquid chromatography/mass spectrometry to determine the molecular weights of the tryptic fragments as an aid in determining the amino acid sequence of the protein.

One of the tryptic fragments of the polypeptide had the same molecular weight and elution time as the C-terminal tryptic fragment of Rs-AFP1 disclosed in PCT Publication No. WO 93/05153, indicating that the two polypeptides share the same C-terminus. None of the other polypeptide tryptic fragment peptide molecular weights matched those of Rs-AFP1, indicating that the present polypeptide is different from Rs-AFP1. Note FIG. 2 in this regard.

EXAMPLE 2

Amino Acid Sequence of AlyAfp

In order to determine the amino acid sequence of AlyAFP, purified polypeptide (greater than 98% pure based on the mass spectrometric data) was denatured in 8M urea containing 8 mM dithiothreitol. Cysteine residues were modified by S-carboxymethylation as described by Stone et al. ((1993) *A Practical Guide To Protein And Peptide Purification For Microsequencing*, P. Matsudaira, Ed., Academic Press, Inc., San Francisco, pp. 55–56). Reagents were removed by dialysis against distilled water using a membrane having a molecular weight cut off of 1,000. Automated Edman degradation was carried out on an Applied Biosystems model 470A Protein Sequenator (Applied Biosystems, Norwalk, Conn.). The respective PTH-amino acid derivatives were identified by reversed phase analysis in an on-line fashion employing an Applied Biosystems Model 120 PTH Analyzer.

N-terminal sequencing of the polypeptide identified 49 amino acids as shown in SEQ ID NO:1, with ambiguous calls at positions 10, 44, 45, and 46. Information derived from mass spectrometric analysis of the tryptic fragments (Example 1) indicated that these undetermined amino acid residues must be tryptophan at position 10, cysteine-isoleucine-cysteine at positions 44-45-46, and cysteine at the 50th and final position.

The complete amino acid sequence of the mature AlyAFP polypeptide is shown in SEQ ID NO:2.

EXAMPLE 3

Bioefficacy of AlyAFP

The antifungal activity of AlyAFP can be expressed as the concentration thereof in $\mu$g/ml required to cause 50% inhibition of fungal hyphal growth ($IC_{50}$). Percent fungal hyphal growth inhibition is defined as 100× the ratio of the average hyphae length in the test sample culture divided by the average hyphae length in the control culture in which buffer is added in place of the polypeptide sample.

The antifungal activity of AlyAFP was determined by measuring the inhibition of fungal hyphal length of a number of different fungi in the presence of this polypeptide under an inverted microscope. Fungal spores ($2\times10^4$ spores/ml) were allowed to germinate for 5 to 15 hours, depending on the fungus used in the test, in 50 $\mu$l of double strength testing medium. The final single strength assay medium contained: $K_2HPO_4$ (2.5 mM), $MgSO_4$ (50 $\mu$M), $CaCl_2$ (50 $\mu$M), $FeSO_4$(5 $\mu$M), $CoCl_2$(0.1 $\mu$M), $CuSO_4$(0.1 $\mu$M), $Na_2MoO_4$(2 $\mu$M), $H_3BO_3$(0.5 $\mu$M), KI (0.1 $\mu$M), $ZnSO_4$(0.5 $\mu$M), $MnSO_4$(0.1 $\mu$M), glucose (10 g/l), asparagine (1 g/l), methionine (20 mg/l), myo-inositol (2 mg/l), biotin (0.2 mg/l), thiamine-HCl (1 mg/l), and pyridoxine-HCl (0.2 mg/l). For experiments on the antagonistic effect of cations, $CaCl_2$ and KCl were added to final concentrations of 1 mM and 50 mM, respectively. This salt-supplemented medium is refered to as "high salt medium," and the original medium is refered to as "low salt medium." After spore germination, 50 $\mu$l of a filter-sterilized solution of polypeptide in distilled water were added to the testing well containing the germinated spores, and the mixture was incubated for 15 to 24 hours at 24° C. AlyAFP was tested in a concentration range from 0 to 80 $\mu$g/ml to determine $IC_{50}$ values. Polypeptide concentrations were determined using the BCA protein assay kit obtained from Pierce (Rockford, Ill.).

Table 1 shows the antifungal activity of AlyAFP against *Fusarium culmorum*, the causal agent of wheat head scab, and *Verticillium dahliae*, the causal agent of early die in potato.

TABLE 1

Antifungal Activity of AlyAFP

| | $IC_{50}$ ($\mu$g/ml) | |
|---|---|---|
| Fungus | Low salt | High salt |
| F. culmorum | <2 | <10 |
| V. dahliae | <1 | <5 |

The data in Table 1 demonstrate that AlyAFP exhibits potent antifungal activity against Fusarium and Verticillium, which cause disease on many crop plants, including barley, corn, cotton, oat, potato, soybean, tomato, and wheat. The antifungal activity of this polypeptide is much less sensitive to the antagonistic effect of salt present in the assay medium compared to that on other antifungal peptides disclosed in PCT International Publication No. WO 93/05153. The concentration in $\mu$g/ml required to cause 50% inhibition of fungal hyphal growth ($IC_{50}$) can be realistically achieved in plants transformed with DNA encoding AlyAFP. These $IC_{50}$ values fall in the range of that of many commercially available fungicides, and reflect the utility of employing this antifungal polypeptide at the infection site on plants.

The data in Table 2 compare the antifungal activity of the present polypetide with that of Rs-AFP1 and Rs-AFP2 disclosed in PCT International Publication WO 93/051553.

TABLE 2

Comparison of the Antifungal Activity of AlyAFP, Rs-AFP1, and Rs-AFP2

| | | $IC_{50}$ ($\mu$g/ml) | |
|---|---|---|---|
| Fungus | Polypeptide | Low salt | High salt |
| F. culmorum | | | |
| | AlyAFP | <2 | <10 |
| | Rs-AFP1 | 5 | 70 |
| | Rs-AFP2 | 2 | 5 |
| V. dahliae | | | |
| | AlyAFP | <1 | <5 |
| | Rs-AFP1 | 5 | >100 |
| | Rs-AFP2 | 1.5 | 50 |

These data demonstrate that the activity of AlyAFP on *F. culmorum* under low salt and high salt conditions is similar to that of Rs-AFP1 and Rs-AFP2. However, the activity of this polypeptide on *V. dahliae* is significantly greater than that of Rs-AFP1 and Rs-AFP2 under high salt conditions.

Figure 4:
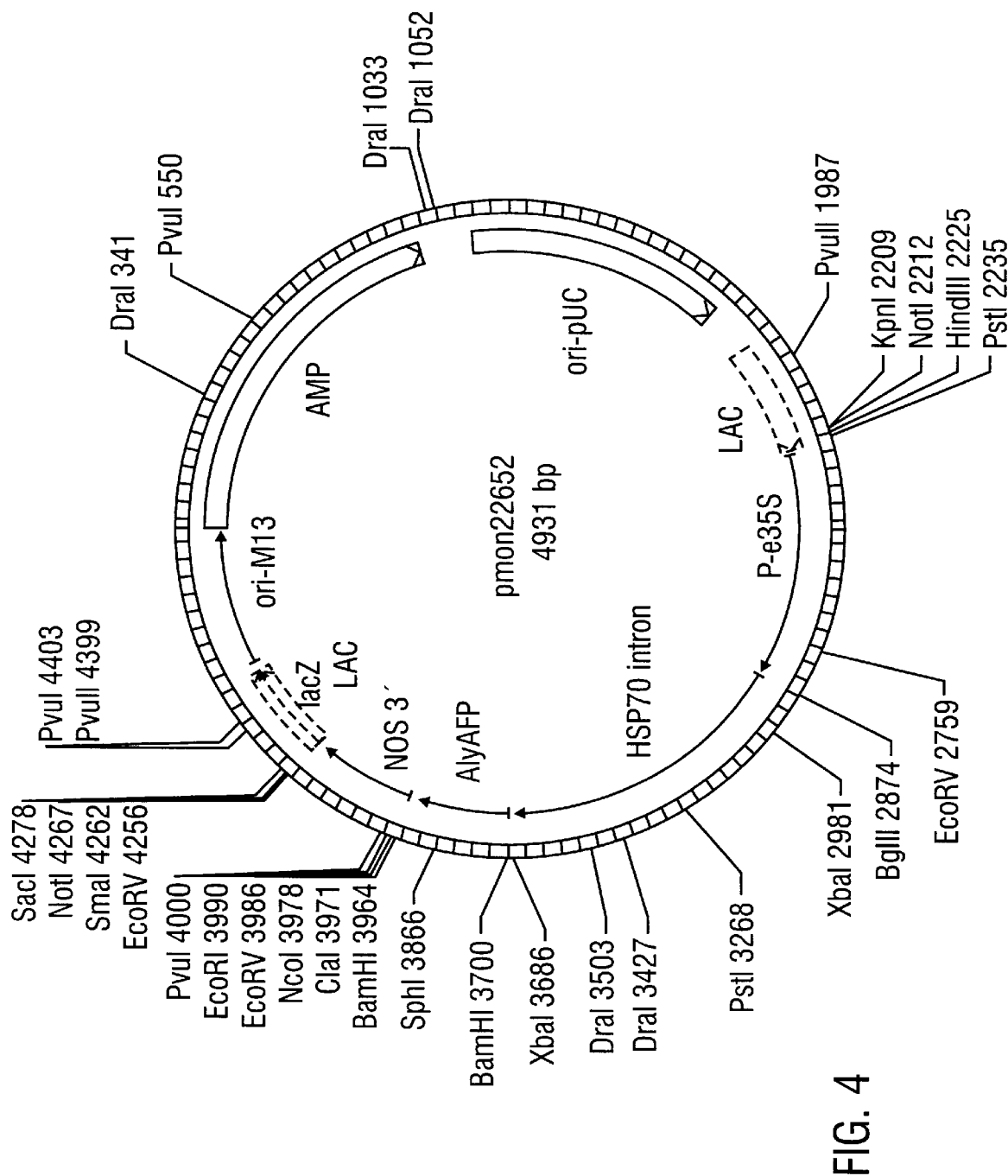
FIG. 4 is a physical map of pMON22652.

AlyAFP and biologically functional equivalents thereof can be used in the control of fungi selected from the following genera and species: Alternaria (*Alternaria brassicola; Alternaria solani*); Ascochyta (*Ascochyta pisi*); Botrytis (*Botrytis cinerea*); Cercospora (*Cercospora kikuchii; Cercospora zaea-maydis*); Colletotrichum (*Colletotrichum lindemuthianum*); Diplodia (*Diplodia maydis*); Erysiphe (*Erysiphe graminis f sp. graminis; Erysiphe graminis f.sp. hordei*); Fusarium (*Fusarium nivale; Fusarium oxysporum; Fusarium graminearum; Fusarium culmorum; Fusarium solani; Fusarium moniliforme; Fusarium roseum*); Gaeumanomyces (*Gaeumanomyces graminis f.sp. tritici*); Helminthosporium (*Helminthosporium turcicum; Helminthosporium carbonum; Helminthosporium maydis*); Macrophomina (*Macrophomina phaseolina; Maganaporthe grisea*); Nectria (*Nectria heamatococca*); Peronospora (*Peronospora manshurica; Peronospora tabacina*); Phoma (*Phoma betae*); Phymatotrichum (*Phymatotrichum omnivorum*); Phytophthora (*Phytophthora cinnamomi; Phytophthora cactorum; Phytophthora phaseoli; Phytophthora parasitica; Phytophthora citrophthora; Phytophthora megasperma f.sp. sojae; Phytophthora infestans*); Plasmopara (*Plasmopara viticola*); Podosphaera (*Podosphaera leucotricha*); Puccinia (*Puccinia sorghi; Puccinia striiformis; Puccinia graminis f.sp. tritici; Puccinia asparagi; Puccinia recondita; Puccinia arachidis*); Puthium (*Puthium aphanidermatum*); Pyrenophora (*Pyrenophora tritici-repentens*); Pyricularia (*Pyricularia oryzae*); Pythium (*Pythium ultimum*); Rhizoctonia (*Rhizoctonia solani; Rhizoctonia cerealis*); Scerotium (*Scerotium rolfsii*); Sclerotinia (*Sclerotinia sclerotiorum*); Septoria (*Septoria lycopersici; Septoria glycines; Septoria nodorum; Septoria tritici*); Thielaviopsis (*Thielaviopsis basicola*); Uncinula (*Uncinula necator*); Venturia (*Venturia inaequalis*); Verticillium (*Verticillium dahliae; Verticillium albo-atrum*)

EXAMPLE 4

Cloning of cDNA Encodine AlyAfp mRNA Isolation

Total RNA was prepared from flowers of Alyssum plants purchased at a local nursery, using the RNaide Plus Kit from Bio 101 Inc. (La Jolla, Calif.) following the protocol suggested by the manufacturer. Polyadenylated RNA was isolated using oligo(dt) cellulose (GIBCO BRL/Life Technologies, Gaithersburg, Md.) as described by Celano et al. (1993) *BioTechniques* 15:27–28.

cDNA Cloning

The 5' region of the polypeptide cDNA was cloned using the 5'-RACE Kit (GIBCO BRL/Life Technologies, Gaithersburg, Md.). First strand cDNA was generated from polyadenylated RNA by reverse transcription using an oligo-dT primer. After removal of the mRNA strand by RNase H1 digestion and spin cartridge separation, a poly-C tail was added to the single stranded cDNA using a terminal deoxynucleotide transferase under conditions recommended by the manufacturer. The 5' region of the polypeptide cDNA was amplified by PCR using the GeneAmp DNA Amplification Reagent Kit (Perkin Elmer Cetus) and the reaction conditions recommended by the manufacturer. The two primers used for amplification were: 1) mixed oligonucleotide 35-mers (14 nucleotides for cloning sites and 21 nucleotides for gene specificity, degeneracy of 24, SEQ ID NO:3) made to amino acids at the C-terminus of the polypeptide sequence in the antisense orientation; and 2) an oligo-dG primer that anneals to the poly-C tail of the cDNA (SEQ ID NO:4). PCR reaction products were analyzed by agarose gel electrophoresis, and a single band of about 250 bp was present in the complete reaction mixture but not in the control reaction mixture that contained only one primer. This band was cut out of the gel and the DNA was isolated using an Ultrafree-MC centrifugation filter unit (Millipore, Bedford, Mass.). The DNA fragment was digested with Bam HI, cloned into the plasmid pGEM11Zf(+) (Promega, Madison, Wis.), and the insert sequenced on a 373 DNA Sequencer Stretch Model from Applied Biosystems using the PRISM Ready Reaction DyeDeoxy Terminator Cycle Sequencing Kit (Applied Biosystems). The sequence is shown in SEQ ID NO:5.

The 3' region of the polypeptide cDNA was cloned as follows. First strand cDNA generated for 5' RACE was used as template for the amplification of the 3' part of the polypeptide cDNA by PCR using the GeneAmp DNA Amplification Reagent Kit (Perkin Elmer Cetus) and the reaction conditions recommended by the manufacturer. The two primers used for amplification were: 1) mixed oligonucleotide 34-mers (14 nucleotides for cloning sites and 20 nucleotides for gene specificity, degeneracy of 16, SEQ ID NO:6) made to amino acid positions 13 to 19 of the polypeptide sequence; and 2) an oligo-dT primer that anneals to the poly(A+) tail of the cDNA (SEQ ID NO:7). PCR reaction products were analyzed by agarose gel electrophoresis, and a single band of about 300 bp was present in the complete reaction mixture but not in the control reaction mixture that contained only one primer. This band was cut out of the gel and the DNA was isolated using an Ultrafree-MC centrifugation filter unit (Millipore). The DNA fragment was digested with Bam Hi, cloned into the plasmid pGEM11Zf(+), and the insert sequenced on a 373 DNA Sequencer Stretch Model from Applied Biosystems using the PRISM Ready Reaction DyeDeoxy Terminator Cycle Sequencing Kit (Applied Biosystems). The sequence is shown in SEQ ID NO:8.

The 5' and 3' regions of the polypeptide cDNA overlapped by 114 nucleotides, and the combination of these two regions provided the sequence of the full length polypeptide cDNA (SEQ ID NO:9).

As shown in FIG. 1, the antifungal polypeptide cDNA encodes a 52 bp 5' leader sequence, a 240 bp open reading frame coding for a 79 amino acid polypeptide, and a 3' untranslated region of 170 bp up to the poly (A+) tail. The deduced polypeptide (FIG. 1) consists of a putative signal peptide of 29 amino acids (underlined in FIG. 1) and a mature polypeptide of 50 amino acids, which is identical to the sequence determined by mass spectrometry analysis and direct amino acid sequencing (see Examples 1 and 2). The amino acid sequence in the vicinity of the predicted signal peptide cleavage site is similar to that of Rs-AFP1 (see FIG. 2), and the actual cleavage occurs between alanine and arginine, i.e., at the arrow in FIG. 1. The resulting unblocked N-terminal end may contribute to the observed superior antifungal activity of the present polypeptide compared to that of Rs-AFP1.

For the convenience of cloning, restriction sites were engineered by PCR into the ends of the cDNA fragment that contained the coding region of the polypeptide cDNA. A 5' gene-specific primer 14 bp upstream of the start codon (ATG) of the prepolypeptide with nested Eco R1 and Bam HI restriction sites (SEQ ID NO:10) and a 3' gene-specific primer after the stop codon (TAA) with nested Eco R1 and Bam H1 restriction sites (SEQ ID NO:11) were used to amplify the cDNA fragment from the cDNAs made by reverse transcription of mRNAs as described above. The PCR amplified fragment is shown in SEQ ID NO:12.

This PCR product was subcloned as a 264 bp Bam HI fragment into the BamHI site of previously constructed *E.* coli cassette vector pMON23317 (FIG. 3) containing an E35S promoter with a maizeHsp70 intron to create pMON22652 (FIG. 4). The 3' nontranslated polyadenylation sequence of the nos gene was provided as the terminator. The vector also contained a multilinker site between the intron and the terminator sequences, NotI sites before and after the promoter and the terminator sequences, and an ampicillin resistance gene. The cDNA insert in pMON22652 was sequenced using a primer (SEQ ID NO:13) made to the sequence of the HSP70 intron 50 bp upstream of the Bam HI cloning site. The sequence of this cDNA insert is shown in SEQ ID NO:14, which is in the correct transcriptional orientation and its deduced amino acid sequence (SEQ ID NO:15) matches that of the polypeptide obtained by direct amino acid sequence analysis (compare SEQ ID NO:2).

Genes encoding AlyAFP, including naturally occurring muteins and variants thereof, presumably exist in the genome of various plant species. These genes can be isolated from the chromosomal DNA of these plant species by conventional molecular biological methods. For example, chromosomal DNA libraries can be constructed in vectors such as the bacteriophage vectors λEMBL3 and λgt10, cosmids, or plasmids using methods known in the art (Sambrook et al. (1989) *Molecular Cloning: A Laboratory Manual*, Cold Spring Harbor Press, Cold Spring Harbor, N.Y.). Genes encoding polypeptides having the same or similar antifungal activity as that of AlyAFP can be isolated by PCR performed on chromosomal DNA or chromosomal DNA libraries, or by probe hybridization of genomic DNA libraries. Primers for PCR and probes for hybridization screening can be designed based on the nucleotide sequence of the polypeptide cDNA shown in SEQ ID NO:12. The primers should not have self-complementary sequences nor have complementary sequences at their 3' ends in order to prevent primer-dimer formation. The primers can contain restriction sites. The primers are annealed to the DNA and sufficient cycles of PCR are performed to yield a product readily visualized by gel electrophoresis and staining. The primers are generally at least 16 nucleotides in length, typically at least 20 nucleotides in length, preferably at least 24 nucleotides in length, and more preferably at least 28 nucleotides in length. Such primers should be capable of specifically priming genes encoding antifungal polypeptides or proteins having the same or similar antifungal activity as AlyAFP. The amplified fragments can be purified and inserted into an appropriate vector, and propagated by conventional means known in the art.

EXAMPLE 5

Peptides, Polypeotides, and Proteins Biolorically Functionally Equivalent to AlyAfp The present invention includes not only the polypeptide having the amino acid sequence shown in SEQ ID NO:2, which can be in the form of an acidic or basic salt, or in neutral form, but also biologically functional equivalent peptides, polypeptides, and proteins. The phrase "biologically functional equivalent peptides, polypeptides, and proteins" denotes peptides, polypeptides, and proteins that contain a sequence or moiety exhibiting sequence similarity to AlyAFP, and which exhibit the same or similar antifungal activity as that of this polypeptide as disclosed herein.

Peptides, Polypehtides, and Proteins Containing Conservative Amino Acid Changes in the Fundamental Polypeptide Sequence Peptides, polypeptides, and proteins biologically functionally equivalent to AlyAFP include amino acid sequences containing conservative amino acid changes in the fundamental sequence shown in SEQ ID NO:2. In such amino acid sequences, one or more amino acids in the fundamental sequence is (are) substituted with another amino acid(s), the charge and polarity of which is similar to that of the native amino acid, i.e., a conservative amino acid substitution, resulting in a silent change.

Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental polypeptide sequence can be made by substituting one amino acid within one of these groups with another amino acid within the same group. Biologically functional equivalents of AlyAFP can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to code for the biologically functionally equivalent form of AlyAFP.

The biologically functional equivalent peptides, polypeptides, and proteins contemplated herein should possess about 70% or greater sequence similarity, preferably about 80% or greater sequence similarity, and most preferably about 90% or greater sequence similarity, to the sequence of, or corresponding moiety within, the fundamental AlyAFP amino acid sequence.

Fragments and Variants of AlyAfp

While the antifungal polypeptide of the present invention preferably comprises the amino acid sequence shown in SEQ ID NO:2, fragments and variants of this sequence possessing the same or similar antifungal activity as that of this antifungal polypeptide are also encompassed by the present invention.

Fragments of AlyAFP

Fragments of AlyAFP can be truncated forms wherein one or more amino acids are deleted from the N-terminal end, C-terminal end, the middle of the polypeptide, or combinations thereof. These fragments can be naturally occurring or synthetic mutants of AlyAFP, and should retain the antifungal activity of AlyAFP.

Variants of AlyAfp

Variants of AlyAFP include forms wherein one or more amino acids has(have) been inserted into the natural sequence. These variants can also be naturally occurring or synthetic mutants of AlyAFP, and should retain the antifungal activity of AlyAFP.

Combinations of the foregoing, i.e., forms of the antifungal polypeptide containing both amino acid deletions and additions, are also encompassed by the present invention. Amino acid substitutions can also be present therein as well.

The fragments and variants of AlyAFP encompassed by the present invention should preferably possess about 70% or greater sequence similarity, more preferably about 80% or greater sequence similarity, and most preferably about 90% or greater sequence similarity, to the corresponding regions of naturally occurring AlyAFP having the amino acid sequence shown in SEQ ID NO:2.

Peptides, Polynentides, and Proteins That React With Antibodies Raised Against AlyAFP Biologically functional equivalent forms of AlyAFP also include peptides, polypeptides, and proteins that react with, i.e., specifically bind to, antibodies raised against AlyAFP, and that exhibit the same or similar antifungal activity as this polypeptide. Such antibodies can be polyclonal or monoclonal antibodies.

Other Biologically Functional Equivalent Forms of AlyAFP

Other biologically functional equivalent forms of AlyAFP useful in the present invention include conjugates of this polypeptide, or biologically functional equivalents thereof as described above, with other peptides, polypeptides, or proteins, forming fusion products therewith exhibiting the same, similar, or greater antifungal activity as compared with that of AlyAFP having the amino acid sequence shown in SEQ ID NO:2. Examples of such peptides, polypeptides, and proteins have been discussed above in the "Summary of the Invention."

EXAMPLE 6

Nucleotide Sequences Biologically Functionally Equivalent to the cDNA Sequence Encoding AlyAfp The present invention includes not only the cDNA sequence shown in SEQ ID NO:12, but also biologically functional equivalent nucleotide sequences. The phrase "biologically functional equivalent nucleotide sequences" denotes DNAs and RNAS, including genomic DNA, plasmid DNA, cDNA, synthetic DNA, and mRNA nucleotide sequences, that encode peptides, polypeptides, and proteins exhibiting the same or similar antifungal activity as that of AlyAFP, i.e., when introduced into host cells in a functionally operable manner so that they are expressed, they produce peptides, polypeptides, or proteins exhibiting antifungal activity at a level sufficient to confer resistance to fungal pathogens upon such cells.

Nucleotide Sequences Encoding Conservative Amino Acid Changes in AlyAfp

Biologically functional equivalent nucleotide sequences of the present invention include nucleotide sequences encoding conservative amino acid changes within the fundamental AlyAFP amino acid sequence, producing silent changes therein. Such nucleotide sequences contain corresponding base substitutions compared to nucleotide sequences encoding wild-type AlyAFP.

Nucleotide Sequences Containing Base Substitutions. Additions, or Deletions

In addition to nucleotide sequences encoding conservative amino acid changes within the fundamental AlyAFP polypeptide sequence, biologically functional equivalent nucleotide sequences of the present invention include nucleotide sequences containing other base substitutions, additions, or deletions. These include nucleic acids containing the same inherent genetic information as that contained in the cDNA of SEQ ID NO:12, and which encode peptides, polypeptides, or proteins conferring fungal resistance the same as or similar to that of AlyAFP upon host cells and plants. Such nucleotide sequences can be referred to as "genetically equivalent modified forms" of the cDNA shown in SEQ ID NO:12, and can be identified by the methods described herein.

Mutations made in the cDNA, plasmid DNA, genomic DNA, synthetic DNA, or other nucleic acid encoding AlyAFP preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, it is not necessary that the nature of the mutations per se be predetermined. For example, in order to select for optimum characteristics of mutants at a given site, random mutagenesis can be conducted at the target codon.

Alternatively, mutations can be introduced at particular loci by synthesizing oligonucleotides containing a mutant sequence, flanked by restriction sites enabling ligation to fragments of the native AlyAFP cDNA sequence. Following ligation, the resulting reconstructed nucleotide sequence encodes a derivative form of AlyAFP having the desired amino acid insertion, substitution, or deletion.

In either case, the expressed mutants can be screened for desired antifungal activity by, for example, the method described in Example 3.

Specific examples of useful genetically equivalent modified forms of the cDNA of SEQ ID NO:12 include DNAs having a nucleotide sequence which exhibits a high level of homology, i.e., sequence identity, to the cDNA of SEQ ID NO:12. This can range from about 70% or greater sequence identity, more preferably from about 80% or greater sequence identity, and most preferably from about 90% or greater sequence identity, to the cDNA or corresponding moiety thereof of SEQ ID NO:12.

Such genetically equivalent modified forms can be readily isolated using conventional DNA-DNA or DNA-RNA hybridization techniques (Sambrook et al. (1989) *Molecular Cloning: A Laboratory Manual*, Second Edition, Cold Spring Harbor Laboratory Press, Cold Spring Harbor, N.Y.) or by amplification using Polymerase Chain Reaction (PCR) methods. These forms should possess the ability to confer resistance to fungal pathogens when introduced by conventional transformation techniques into plant cells normally sensitive to such pathogens.

Nucleotide Sequences Encoding Fragments and Variants of AlyAfp

The fragments and variants of AlyAFP discussed in Example 5 can be encoded by cDNA, plasmid DNA, genomic DNA, synthetic DNA, or mRNA. These nucleic acids should possess about 70% or greater sequence similarity, preferably about 80% or greater sequence similarity, and most preferably about 90% or greater sequence similarity, to corresponding regions or moieties of the cDNA having the nucleotide sequence shown in SEQ ID NO:12 encoding AlyAFP, or the mRNA corresponding thereto.

In the present invention, nucleic acids biologically functional equivalent to the cDNA of AlyAFP having the nucleotide sequence shown in SEQ ID NO:12 include:

(1) DNAs having a length which has been altered either by natural or artificial mutations such as partial nucleotide deletion, insertion, addition, or the like, so that when the entire length of SEQ ID NO:12 is taken as 100%, the biologically functional equivalent sequence has an approximate length of 60–120% of that of SEQ ID NO:12, preferably 80–110% thereof; or (2) nucleotide sequences containing partial (usually 20% or less, preferably 10% or less, more preferably 5% or less of the entire length) natural or artificial mutations so that such sequences code for different amino acids, but wherein the resulting polypeptide retains the antifungal activity of AlyAFP. The mutated DNAs created in this manner usually encode a polypeptide having 70% or greater, preferably 80% or greater, and more preferably 90% or greater, sequence identity to the amino acid sequence of AlyAFP (SEQ ID NO:2) encoded by the nucleotide sequence of SEQ ID NO:12.

In the present invention, the methods employed to create artificial mutations are not specifically limited, and such mutations can be produced by any of the means conventional in the art.

For example, the cDNA or gene of AlyAFP can be treated with appropriate restriction enzymes so as to insert or delete appropriate DNA fragments so that the proper amino acid reading frame is preserved. Subsequent to restriction endonuclease treatment, the digested DNA can be treated to fill in any overhangs, and the DNA religated.

Mutations can also be introduced at particular loci by synthesizing oligonucleotides containing a mutant sequence flanked by restriction sites enabling ligation to fragments of the native AlyAFP cDNA or genomic sequence. Following ligation, the resulting reconstructed sequence encodes a derivative having the desired amino acid insertion, substitution, or deletion.

Alternatively, oligonucleotide-directed site-specific or segmentspecific mutagenesis procedures can be employed to produce an altered cDNA or genomic DNA sequence having particular codons altered according to the substitution, deletion, or insertion desired.

Exemplary methods of making the alterations described above are disclosed by Ausubel et al. (1995) *Current Protocols in Molecular Biology*, John Wiley & Sons, Inc.; Bauer et al. (1985) *Gene* 37:73; Craik (1985) *BioTechniques* 3:12–19; Frits Eckstein et al. (1982) *Nucleic Acids Research* 10:6487–6497; Sambrook et al. (1989) *Molecular Cloning: A Laboratory Manual*, Second Edition, Cold Spring Harbor Laboratory Press, Cold Spring Harbor, N.Y.; Smith et al. (1981) In *Genetic Engineering: Principles and Methods*, Setlow et al., Eds., Plenum Press, N.Y., pp. 1–32; Osuna et al. (1994) *Critical Reviews In Microbiology*, 20:107–116; and Walder et al. (1986) *Gene* 42:133. Biologically functional equivalents to the cDNA sequence disclosed herein produced by any of these methods can be selected for by assaying the peptide, polypeptide, or protein encoded thereby using the techniques described in Example 3.

Nucleotide Sequences Encoding Peptides, polypeptides. and Proteins That React With Antibodies Raised Against AlyAfp Biologically functional equivalent forms of the CDNA encoding AlyAFP include nucleotide sequences that encode peptides, polypeptides, and proteins that react with, i.e., specifically bind to, antibodies raised against AlyAFP, and that exhibit the same or similar antifungal activity as this polypeptide. Such antibodies can be polyclonal or monoclonal antibodies.

Genetically Degenerate Nucleotide Sequences

Due to the degeneracy of the genetic code, i.e., the existence of more than one codon for most of the amino acids naturally occurring in proteins, other DNA (and RNA) sequences that contain essentially the same genetic information as the cDNA of the present invention, and which encode substantially the same amino acid sequence as that encoded by the nucleotide sequence of SEQ ID NO:12, can be used in practicing the present invention. This principle applies as well to any of the other nucleotide sequences discussed herein.

Synthetic DNA Sequences Designed for Enhanced Expression in Particular Host Cells Biologically functional equivalent forms of the cDNA of the present invention also include synthetic DNAs designed for enhanced expression in particular host cells. Host cells often display a preferred pattern of codon usage (Murray et al. (1989) *Nucl. Acids. Res.* 17:477–498). Synthetic DNAs designed to enhance expression in a particular host should therefore reflect the pattern of codon usage in the host cell.

In the present invention, sequence similarity or identity can be determined using the "BestFit" or "Gap" programs of the Sequence Analysis Software Package, Genetics Computer Group, Inc., University of Wisconsin Biotechnology Center, Madison, Wis. 53711.

Nucleotide Sequences Encoding Fused Forms of AlyAfp

Other biologically functional equivalent forms of the cDNA of SEQ ID NO:12 useful in the present invention include those which have been modified to encode conjugates with other peptides, polypeptides, or proteins such as those discussed under "Summary of the Invention" and in Example 5, thereby encoding fusion products therewith.

Biologically Functional Equivalent Forms of AlyAfp cDNA Detected by Hybridization Although one embodiment of a nucleotide sequence encoding AlyAFP is shown in SEQ ID NO:12, it should be understood that the present invention also includes nucleotide sequences that hybridize to the sequence of SEQ ID NO:12 and its complementary sequence, and that code on expression for peptides, polypeptides, or proteins having the same or similar antifungal activity as that of AlyAFP. Such nucleotide sequences preferably hybridize to SEQ ID NO:12 or its complementary sequence under conditions of moderate to high stringency (see Sambrook et al. (1989) *Molecular Cloning: A Laboratory Manual*, Second Edition, Cold Spring Harbor Laboratory Press, Cold Spring Harbor, N.Y.). Exemplary conditions include initial hybridization in 6× SSC, 5× Denhardt's solution, 100 µg/ml fish sperm DNA, 0.1% SDS, at 55° C. for sufficient time to permit hybridization (e.g., several hours to overnight), followed by washing two times for 15 min each in 2× SSC, 0.1% SDS, at room temperature, and two times for 15 min each in 0.5–1× SSC, 0.1% SDS, at 55° C., followed by autoradiography. Typically, the nucleic acid molecule is capable of hybridizing when the hybridization mixture is washed at least one time in 0.1× SSC at 55° C., preferably at 60° C., and more preferably at 65° C.

The present invention also encompasses nucleotide sequences that hybridize to the cDNA of SEQ ID NO:12 under salt and temperature conditions equivalent to those described above, and that code on expression for a peptide, polypeptide, or protein that has the same or similar antifungal activity as that of AlyAFP disclosed herein.

The nucleotide sequences described above are considered to possess a biological function substantially equivalent to that of the cDNA of SEQ ID NO:12 encoding AlyAFP if they encode peptides, polypeptides, or proteins having an antifungal effect differing from that of AlyAFP by about ±25% or less.

Genomic Probes and PCR Primers

Genomic Probes

In another aspect, the present invention provides oligonucleotide hybridization probes useful in screening genomic and other nucleic acid libraries for DNA sequences encoding peptides, polypeptides, and proteins having antifungal activity the same or similar to that of AlyAFP, which probes can be designed based on the sequences provided herein. Such probes can range from about 16 to about 28 nucleotides in length, generally about 16 nucleotides in length, more typically about 20 nucleotides in length, preferably about 24 nucleotides in length, and more preferably about 28 nucleotides in length. Preferably, these probes specifically hybridize to genomic DNA and other DNA sequences encoding peptides, polypeptides, or proteins having the same or similar antifungal activity as that of AlyAFP. Such oligonucleotide probes can be synthesized by automated synthesis, and can be conveniently labeled at the 5' end with a reporter molecule such as a radionuclide, e.g., $^{32}$P, or biotin. The library can be plated as colonies or phage, depending upon the vector employed, and the recombinant DNA is transferred to nylon or nitrocellulose membranes. Following denaturation, neutralization, and fixation of the DNA to the membrane, the membrane is hybridized with the labeled probe. Following this, the membrane is washed, and the reporter molecule detected. Colonies or phage harboring hybridizing DNA are then isolated and propagated. Candidate clones or PCR-amplified fragments can be verified as comprising DNA encoding AlyAFP or related peptides, polypeptides, or proteins having antifungal activity the same as or similar to that of AlyAFP by a variety of means. For example, the candidate clones can be hybridized with a second, non-overlapping probe, or subjected to DNA sequence analysis. The antifungal activity of the peptide, polypeptide, or protein encoded thereby can be assessed by cloning and expression of the DNA in an appropriate host such as yeast or E. coli, followed by isolation of the peptide, polypeptide, or protein, and assay of the antifungal activity thereof by the method described in Example 3, above. By such means, plant nucleic acids encoding AlyAFP, or peptides, polypeptides, or proteins biologically functionally equivalent thereto, useful in controlling undesired fungi and protecting plants against fungal pathogens can be isolated.

PCR Primers

Biologically functional equivalent genomic DNAs and cDNAs can be isolated from organisms including higher plants using degenerate oligonucleotide primers based on the amino acid sequence (SEQ ID NO:2) of AlyAFP (T. Compton (1990) In Innis et al., Eds., *PCR Protocols, A Guide to Methods and Applications*, Academic Press, San Diego, pp. 39–45). Such degenerate oligonucleotide primers can be used in conjunction with PCR technology employing reverse transcriptase to amplify biologically functionally equivalent cDNAs (E.S. Kawasaki (1990) In Innis et al., Eds., *PCR Protocols, A Guide to Methods and Applications*, Academic Press, San Diego, pp. 21–27). These cDNAs can then be easily cloned in appropriate transformation/expression vectors and introduced into monocots and dicots, and transformed plants expressing the DNAs in these vectors can be isolated using established procedures as discussed below.

The degenerate oligonucleotides can be used to screen genomic libraries directly, and the isolated coding sequences can be transferred into transformation/expression vectors for crop plants.

Alternatively, the degenerate oligonucleotides can be used as probes to screen cDNA libraries from plants in, for example, λ phage vectors such as λ ZapII (Stratagene, La Jolla, Calif.). The cDNA isolated in this manner can be transferred to an appropriate transformation/expression vector for introduction into monocot or dicot plants as described below.

EXAMPLE 6

DNA Constructs for Expression of AlyAfp in Transgenic Plants

As noted above, the present invention provides DNA constructs or expression vectors that facilitate the expression of the DNA sequences discussed herein in higher plants and various microorganisms. As used herein, the terms "vector construct" or "expression vector" refer to assemblies of DNA fragments operatively linked in a functional manner that direct the expression of the DNA sequences discussed herein, as well as any additional sequence(s) or gene(s) of interest.

The expression of a plant structural coding sequence (gene, cDNA, synthetic DNA, or other DNA) which exists in double-stranded DNA form involves transcription of messenger RNA (mRNA) from one strand of the DNA by RNA polymerase enzyme and subsequent processing of the mRNA primary transcript inside the nucleus. This processing involves a 3' non-translated region which adds polyadenylate nucleotides to the 3' end of the mRNA.

Transcription of DNA into mRNA is regulated by a region of DNA referred to as the "promoter." The promoter region contains a sequence of bases that signals RNA polymerase to associate with the DNA and initiate transcription of mRNA using one of the DNA strands as a template to make a corresponding strand of RNA.

Vectors useful in the present invention therefore include promoter elements operably linked to coding sequences of interest, and can also include 5' non-translated leader sequences, 3' non-translated regions, and one or more selectable markers. A variety of such markers are well known in the art.

Promoters

The expression of DNA encoding AlyAFP in plant cells can be placed under the control of the naturally occurring homologous promoter, or a variety of heterologous promoters. A number of promoters active in plant cells have been described in the literature. These include, for example, the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel et al. (1995) *Plant Mol. Biol.* 29: 995–1004); the chitinase promoter from Arabidopsis (Samac et al. (1991) *Plant Cell* 3: 1063–1072); the LTP (Lipid Transfer Protein) promoters from broccoli (Pyee et al. (1995) *Plant J.* 7:49–59); the ubiquitin promoter from maize (Christensen et al. (1992) *Plant Mol. Biol.* 18:675–689); and the actin promoter from rice (McElroy et al. (1990) *Plant Cell* 2:163–171). All of these promoters have been used to create various types of DNA constructs that have been expressed in plants. See, for example, PCT International Publication WO 84/02913 in this regard.

Promoters useful in double-stranded DNA constructs of the present invention can be selected based upon their ability to confer specific expression of a coding sequence in response to fungal infection. The infection of plants by fungal pathogens triggers the induction of a wide array of proteins, termed defense-related or pathogenesis-related (PR) proteins (Bowles (1990) *Ann. Rev. Biochem.* 59:873–907; Bol et al. (1990) *Ann. Rev. Phytopathol.* 28:113–138; Linthorst (1991) *Crit. Rev. Plant Sci.* 10:123–150). Such defense-related or PR genes may encode enzymes involved in phenylpropanoid metabolism (e.g., phenylalanine ammonia lyase, chalcone synthase), proteins that modify plant cell walls (e.g., hydroxyproline-rich glycoproteins, glycine-rich proteins, peroxidases), enzymes that degrade fungal cell walls (e.g., chitinases, glucanases), thaumatin-like proteins, or proteins of as yet unknown function. Defense-related or PR genes have been isolated and characterized from a number of plant species. The promoters of these genes can be used to drive expression of AlyAFP and biologically functional equivalents thereof in transgenic plants challenged with fungal pathogens. For example, such promoters have been derived from defense-related or PR genes isolated from potato plants (Fritzemeier et al. (1987) *Plant Physiol.* 85:34–41; Cuypers et al. (1988) *Mol. Plant-Microbe Interact.* 1:157–160; Logemann et al. (1989) *Plant Cell* 1:151–158; Matton et al. (1989) *Mol. Plant-Microbe Interact.* 2:325–331; Schroder et al. (1992) *Plant J.* 2:161–172). Alternatively, pathogen-inducible promoters such as the PRP1 promoter obtainable from tobacco (Martini et al. (1993) *Mol. Gen. Genet.* 263:179) can be employed.

Promoters useful in the the double-stranded DNA constructs of the present invention can also be selected based upon their ability to confer specific expression in tissues where AlyAFP protein is most effective, such as in the flowering parts of the plant (Weigel (1995) *Annu. Rev. Genetics* 29:19–39).

In any case, the particular promoter selected to drive the expression of AlyAFP in transgenic plants should be capable of causing sufficient expression of the this polypeptide coding sequence to result in the production of an antifungal effective amount of AlyAFP in plant tissues. Examples of constitutive promoters capable of driving such expression are the e35S, FMV35S, rice actin, maize ubiquitin, and eIF-4A promoters.

The promoters used in the DNA constructs of the present invention can be modified, if desired, to affect their control characteristics. For example, the CaMV35S promoter can be ligated to the portion of the ssRUBISCO gene that represses the expression of ssRUBISCO in the absence of light, thereby creating a promoter active in leaves but not in roots. For purposes of the present invention, the phrase "CaMV35S" promoter includes variations of the CaMV35S promoter, e.g., promoters derived by means of ligation with operator regions, random or controlled mutagenesis, etc. Furthermore, promoters useful in the present invention can be altered to contain multiple enhancer sequences to assist in elevating the level of gene expression. Examples of such enhancer sequences have been reported by Kay et al. ((1987) *Science* 236:1299).

5' Non-translated Leader Sequences

The RNA produced by DNA constructs of the present invention should also preferably contain a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. However, the present invention is not limited to constructs wherein the 5' non-translated region is derived from the 5' non-translated sequence that accompanies the promoter sequence. Rather, the non-translated leader sequence can be derived from an unrelated promoter or coding sequence. For example, the petunia heat shock protein 70 (Hsp70) contains such a leader (Winter (1988) *Mol. Gen. Genet.* 221:315–319).

3' Non-translated Regions

As noted above, the 3' non-translated region of the chimeric constructs of the present invention should contain a transcriptional terminator, or an element having equivalent function, and a polyadenylation signal that functions in plants to cause the addition of adenylate nucleotides to the 3' end of the mRNA. Examples of such 3' regions include the 3' transcribed, nontranslated regions containing the polyadenylation signal of Agrobacterium tumor-inducing (Ti) plasmid genes, such as the nopaline synthase (nos) gene, and plant genes such as the soybean 7s storage protein gene and pea ssRUBISCO E9 gene (Fischoff et al., European Patent Application 0 385 962).

All the foregoing elements are combined to provide a recombinant, double-stranded DNA molecule, comprising operatively linked in the 5' to 3' direction:

a) a promoter that functions in plant cells to cause the production of an RNA sequence;

b) a DNA coding sequence that encodes AlyAFP; and c) a 3' non-translated region that functions in plant cells to cause transcriptional termination and the addition of polyadenylate nucleotides to the 3' end of said RNA sequence.

The AlyAFP DNA coding sequence can comprise the entire nucleotide sequence shown in SEQ ID NO:12, or can comprise nucleotides 116 to 269 of SEQ ID NO:12. In the former case, AlyAFP will be transported to the extracellular space; in the latter case, it will accumulate within the cells of the plant. In either case, AlyAFP will be effective in controlling fungal damage.

EXAMPLE 7

Production of Transgenic Potato Plants Expressing AlyAfp and Results of Disease Tests for Verticillium Wilt Control The research described herein has identified cDNAs and other nucleic acids that are able to confer resistance to fungal pathogens onto plants. Agronomic, horticultural, ornamental, and other economically or commercially useful plants can be made resistant to fungal pathogens by introducing these DNAs therein in a functionally operable manner so that they are expressed at a level effective to confer resistance to fungal pathogens upon these plants.

Transgenic plants that express antifungal effective amounts of AlyAFP and biologically functional equivalents thereof can be produced by:

(a) transforming plant cells with a recombinant DNA molecule comprising operatively linked in sequence in the 5' to 3' direction:

(i) a promoter region that directs the transcription of a gene in plants;

(ii) a DNA coding sequence that encodes an RNA sequence which encodes AlyAFP or a biologically functionally equivalent thereof having the same or similar antifungal activity as that of AlyAFP; and (iii) a 3' non-translated region that encodes a polyadenylation signal which functions in plant cells to cause transcriptional termination and the addition of polyadenylate nucleotides to the 3' end of said RNA sequence;

(b) selecting plant cells that have been transformed;

(c) regenerating plant cells that have been transformed to produce differentiated plants; and (d) selecting a transformed plant, cells of which express said DNA coding sequence and produce an antifungal effective amount of AlyAFP or said biologically functionally equivalent thereof.

Alyssum, from which AlyAFP was originally isolated, is a dicot. As discussed by Campbell et al. ((1990) *Plant Physiol.* 92:1–11), while a clear difference in codon usage patterns exists between monocots and dicots, it is known that monocots express genes resembling those found in dicots. Based on this observation, it appears that codon usage in dicot genes would not present a great barrier to expression of dicot genes in monocots. In any event, those of ordinary skill in the art are familiar with the principles governing the adaptation of codon usage to suit the host plant (see Murray et al. (1989) Nucl. Acids. Res. 17:477–498), and the expression of DNA constructs is now routine in the art.

A summary of the literature reporting the production of transgenic monocotyledonous and dicotyledonous plants is as follows.

Monocot Transformation

Methods for producing transgenic plants among the monocots are currently available. Successful transformation and plant regeneration have been achieved in asparagus (*Asparagus officinalis*; Bytebier et al. (1987) *Proc. Natl. Acad. Sci. USA* 84:5345); barley (*Hordeum vulgare*; Wan and Lemaux (1994) *Plant Physiol.* 104:37); maize (*Zea mays*; Rhodes et al. (1988) *Science* 240:204; Gordon-Kamm et al. (1990) *Plant Cell* 2:603; Fromm et al. (1990) *Bio/Technology* 8:833; Koziel et al. (1993) *Bio/Technology* 11:194); oats (*Avena sativa*; Somers et al. (1992) *Bio/Technology* 10:1589); orchardgrass (*Dactylis glomerata*; Horn et al. (1988) *Plant Cell Rep.* 7:469); rice (*Oryza sativa*, including indica and japonica varieties; Toriyama et al. (1988) *Bio/Technology* 6:10; Zhang et al. (1988) *Plant Cell Rep.* 7:379; Luo and Wu (1988) *Plant Mol. Biol. Rep.* 6:165; Zhang and Wu (1988) *Theor. Appl. Genet.* 76:835; Christou et al. (1991) *Biol/Technology* 9:957); rye (*Secale cereale*; De la Pena et al. (1987) *Nature* 325:274); sorghum (*Sorghum bicolor*; Cassas et al. (1993) *Proc. Natl. Acad. Sci. USA* 90:11212); sugar cane (*Saccharum spp.*; Bower and Birch (1992) *Plant J.* 2:409); tall fescue (*Festuca arundinacea*; Wang et al. (1992) *Biol/Technology* 10:691); turfgrass (*Agrostis palustris*; Zhong et al. (1993) *Plant Cell Rep.* 13:1); wheat (*Triticum aestivum*; Vasil et al. (1992) *Bio/Technology* 10:667; Troy Weeks et al. (1993) *Plant Physiol.* 102:1077; Becker et al. (1994) *Plant J.* 5:299).

The DNAs encoding AlyAFP or biologically functional equivalents thereof discussed herein can be introduced into any of these plants in order to produce transgenic plants that express an antifungal effective amount of AlyAFP.

Dicot Transformation

Methods for transforming a wide variety of different dicots and obtaining transgenic plants are well documented in the literature (see Gasser and Fraley (1989) *Science* 244:1293; Fisk and Dandekar (1993) *Scientia Horticulturae* 55:5–36; Christou (1994) *Agro Food Industry Hi Tech* (March/April 1994) p.17, and the references cited therein).

The DNAs encoding AlyAFP or biologically functional equivalents thereof discussed herein can be introduced into any of these plants in order to produce transgenic plants that express an antifungal effective amount of AlyAFP.

By way of non-limiting example, cDNA encoding AlyAFP has been expressed in potato plants, conferring fungal resistance thereto, as described in detail below.

Plasmids for Potato Transformation

Figure 5:
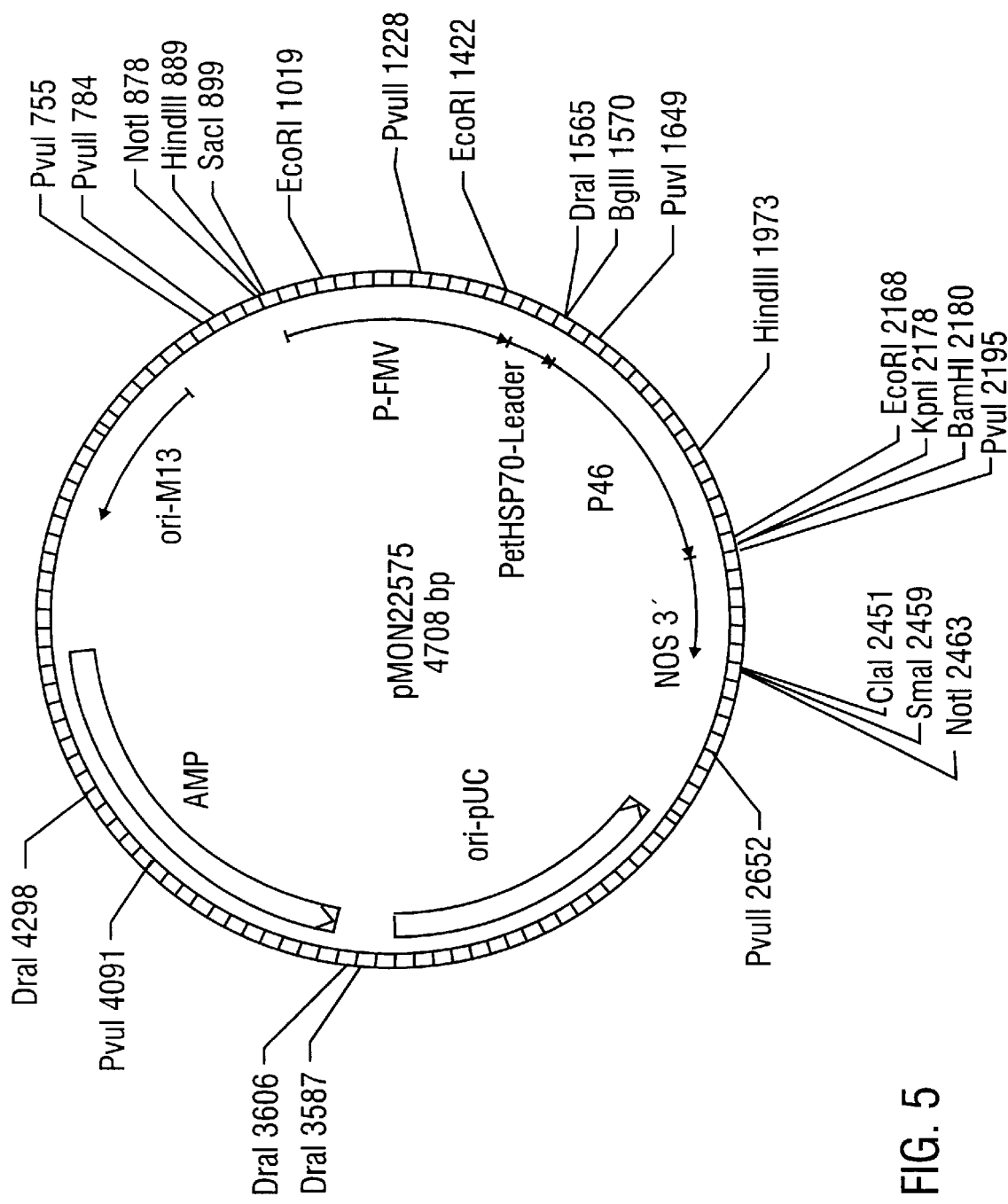
FIG. 5 is a physical map of pMON22575.
Figure 6:
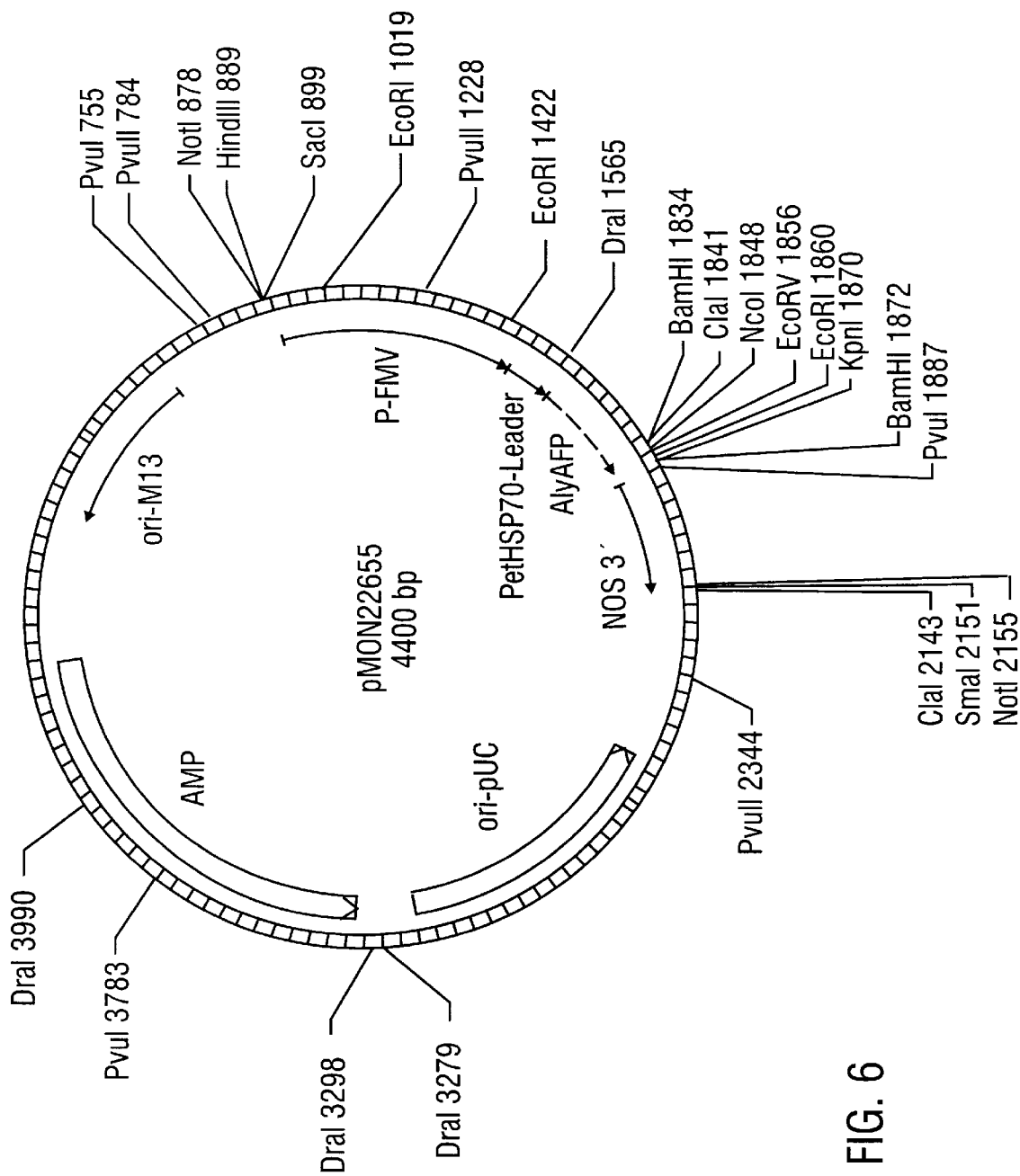
FIG. 6 is a physical map of pMON22655.

The 290 bp Bam H1/Eco RI fragment encoding AlyAFP was cloned from plasmid pMON22652 (FIG. 4) into previously constructed *E. coli* cassette vector pMON22575 (FIG. 5), replacing the p46 gene therein. The resulting plasmid, designated pMON22655 (FIG. 6), was cleaved with Not I to isolate the Not I fragment containing the polypeptide-encoding cDNA. This Not I fragment was subsequently inserted into the Not I site of pMON17227 (FIG. 7), a double border plant transformation vector. The resulting plasmid was designated pMON22657 (FIG. 8), and contains DNA fragments as follows: The bacterial spectinomycin/streptomycin resistance gene (Spc/Str) (Fling et al. (1985) *Nucl. Acids Res.* 13:7095–7106), followed by the right border of the T-DNA. Adjacent to the right border is the synthetic bacterial glyphosate resistance CP4 5-enolpyruvyl-3-phosphoshikimate synthase (EPSPS) gene driven by the FMV promoter (see PCT publication WO92/04449). The CP4 gene confers glyphosate resistance to the transformants, and thus the capability of using glyphosate as the means for selecting transformants. A chloroplast transit peptide from the Arabidopsis 5-enopyruvyl-3-phosphoshikimate synthase gene(EPSPS) was fused to the CP4 gene to target the CP4-EPSPS protein to the chloroplasts. At the 3' end of the CP4 gene is the E9 3' end that provides a transcriptional termination site and polyadenylation signal sequence. The next chimeric segments consist of the FMV promoter, the antifungal polypeptide cDNA, and the nos 3' end. This is followed by the left border of the T-DNA, and the origin of replication (ori-322) (Stalker et al. (1981) *Mol. Gen. Genet.* 181:8–12).

Figure 9:
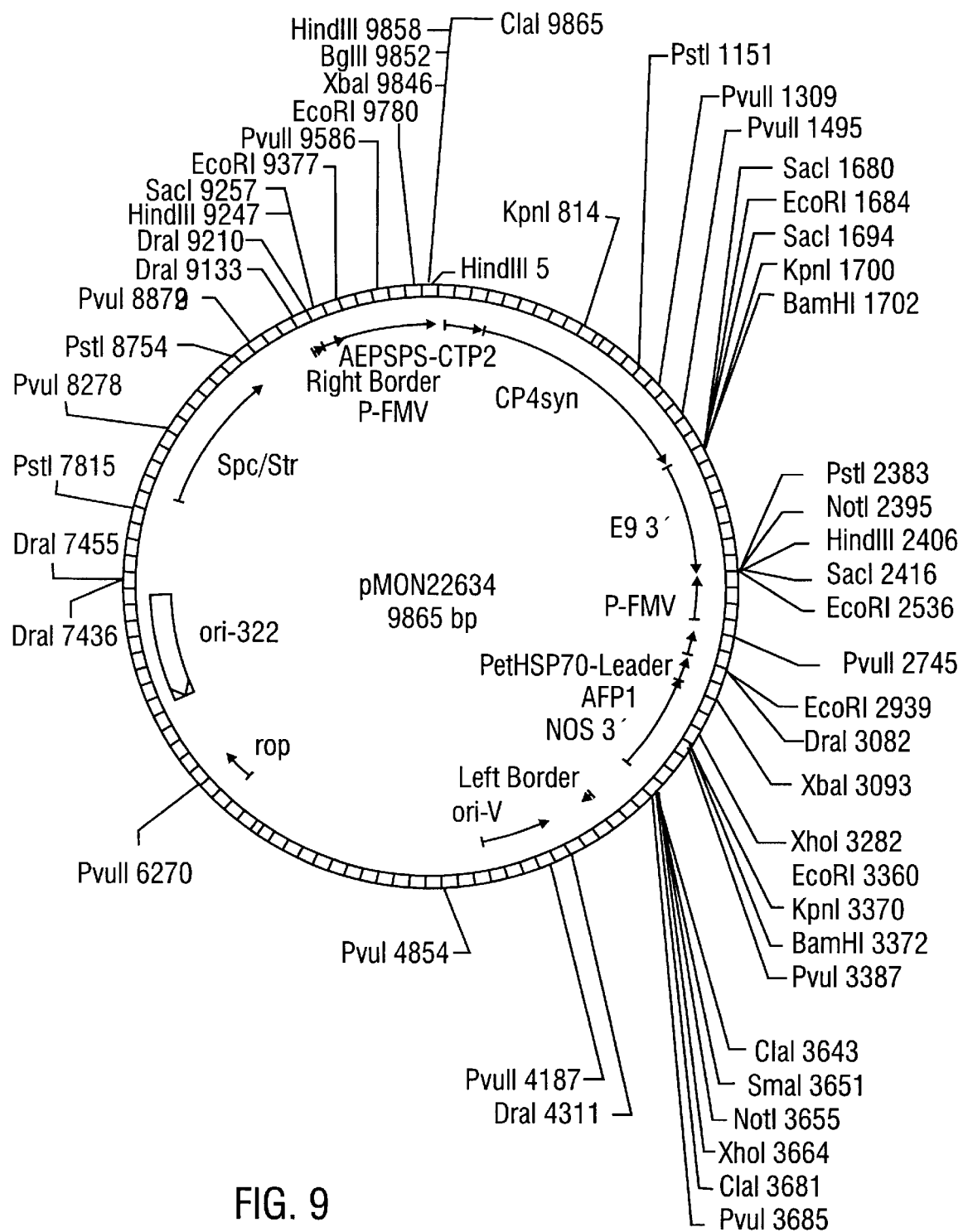
FIG. 9 is a physical map of pMON22634.
Figure 10:
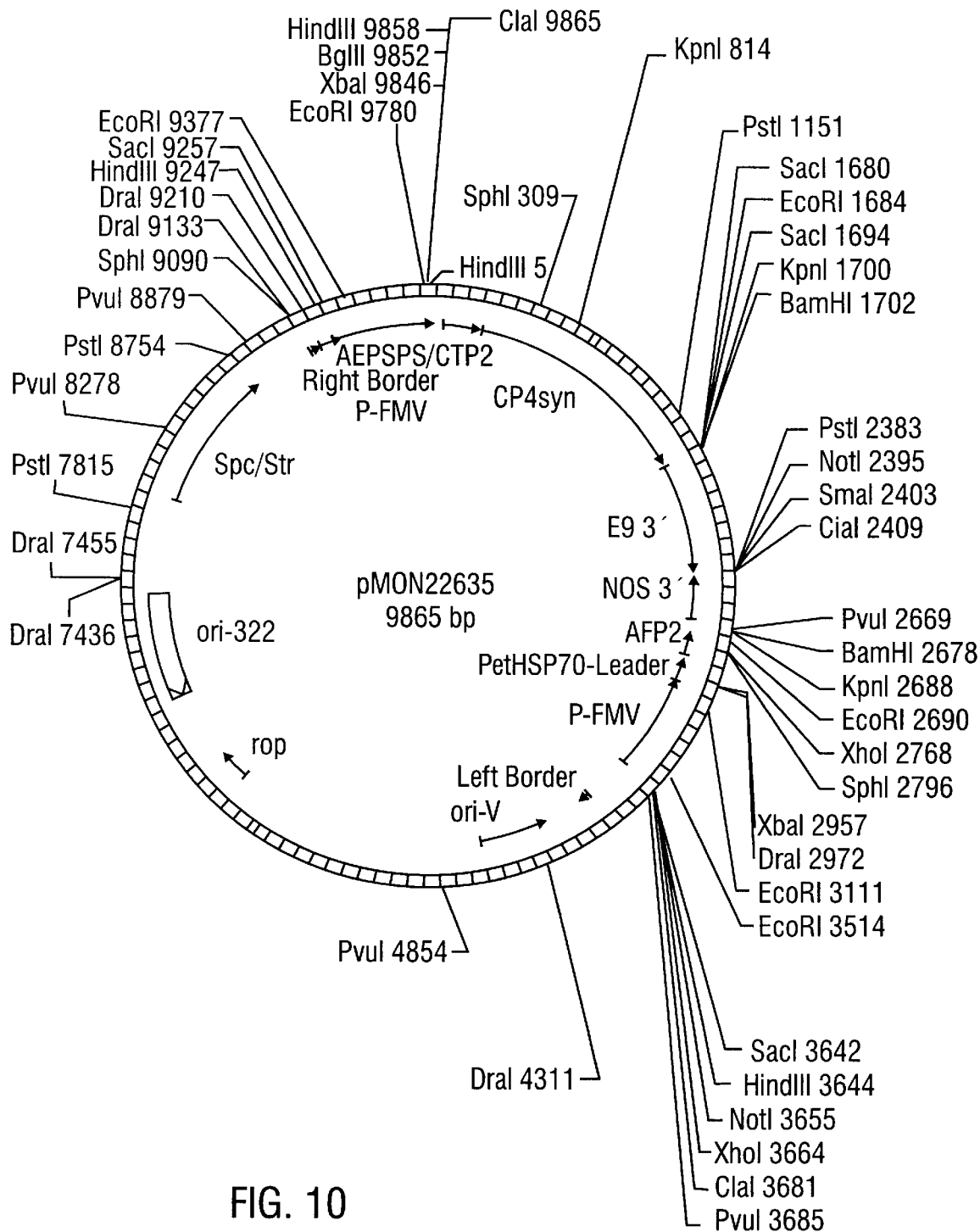
FIG. 10 is a physical map of pMON22635.

For the purpose of comparing the in planta antifungal activity of AlyAFP with that of Rs-AFP1 and Rs-AFP2, Rs-AFP1 and Rs-AFP2 synthetic DNAs were also transformed into potato plants. Rs-AFP1 and Rs-AFP2 synthetic DNAs were chemically synthesized by Midland Certified (Midland, Tex.) as 273 bp Bam HI/Eco RI fragments (SEQ ID NO:16 and SEQ ID NO:17, respectively), and were first cloned into previously constructed *E. coli* cassette vector pMON22575 (FIG. 5), replacing the p46 gene therein. Not I fragments containing Rs-AFP1 and Rs-AFP2 DNAs were independently cloned into the plant transformation vector pMON17227 (FIG. 7) by the same procedure used for cloning the cDNA of AlyAFP. The resulting plasmids were designated pMON22634 (Rs-AFP1) (FIG. 9) and pMON22635 (Rs-AFP2) (FIG. 10).

Triparental Mating Procedure

Prior to transformation, *E. coli*, each containing pMON22657, pMON22634, or pMON22635, respectively, were mated with Agrobacterium ABI by a triparental mating procedure with *E. coli* harboring the helper plasmid pRK2013 (Ditta et al. (1980) *Proc. Natl. Acad. Sci. USA* 77:7347). ABI is the A208 *Agrobacterium tumefaciens* strain carrying the disarmed pTiC58 plasmid pMP90RK (Koncz et al. (1986) *Mol. Gen. Genet.* 204:383–396). The disarmed Ti plasmid provides the trfA gene functions that are required for autonomous replication of the pMON vectors after conjugation into the ABI strain. When plant tissue is incubated with the ABI::pMON conjugates, the vectors are transferred to the plant cells by the vir functions encoded by the disarmed pMP90RK Ti plasmid.

Agrobacterium were grown for 30 hours at 30° C. in LB medium (10 g tryptone, 5 g yeast extract, and 5 g NaCl per liter) containing 25 µg/ml chloramphenicol and 50 mg/ml kanamycin. *E. coli* containing pRK2013 were grown overnight in LB medium containing 50 µg/ml kanamycin. *E. coli* harboring pMON22657, pMON22634, and pMON22635 were grown in LB medium containing 75 µg/ml spectinomycin. After all of the cultures were grown, 4 mls of LB medium were added to a tube containing 100 µl each of Agrobacterium ABI, *E. coli*/pRK2013, and *E. coli*/pMON. This mixture was centrifuged in a microfuge for 1 min., and the supernatant fraction decanted. The pellet fraction was resuspended in the remaining liquid (approximately 100 µl), and an aliquot (approximately 25 µl) was pipetted onto the center of an LB agar (1.5%) plate. After growth overnight at 30° C., an aliquot of cells from this plate was streaked onto an LB agar plate supplemented with 75 μg/ml spectinomycin, 50 μg/ml kanamycin, and 25 μg/ml chloramphenicol.

After 24–48 hours at 30° C., colonies were present on the plate streaked with cells resulting from the triparental mating of E. coli containing a pMON plasmid, E. coli containing pRK2013, and Agrobacterium ABI, while no colonies were present on the control plate streaked with cells from the mating of the pMON-containing E. coli and ABI (without E. coli containing pRK2013, which is required for plasmid mobilization). After the triparental mating, 4 colonies were selected from the former plate, and each was separately inoculated into a liquid culture of LB supplemented with 75 μg/ml spetinomycin, 50 μg/ml kanamycin, and 25 μg/ml chloramphenicol, and grown at 30° C. The presence of the DNA encoding the different antifungal polypeptides was confirmed by restriction analysis of plasmid DNA isolated from the Agrobacterium cells. Cultures containing DNAs encoding AlyAFP, Rs-AFP1, and Rs-AFP2, respectively, were individually used for transformation of potato plants.

Transformation of Potato Plants

Agrobacterium containing pMON22657, pMON22634, and pMON22635, respectively, were grown overnight in 2 mls of LB medium containing 75 μg/ml spectinomycin, 25 μg/ml chloramphenicol, and 50 μg/ml kanamycin, pH 7.0. The following day, the bacteria were diluted 1:10 with MSO medium containing 4.4 g MS salts (Sigma Chemical Co., St. Louis, Mo.), 30 g sucrose, and 2 mls vitamin B5 (Sigma catalogue # G 1019) in a 1 liter volume, pH 5.7, or until an optical density reading of 0.2–0.33 at 600 nm was obtained.

Leaves were removed from the stems of potato plants (*Solanum tuberosum* var. Russet Burbank) that had been grown from stem cuttings containing nodes under sterile conditions, including a temperature of 19° C., a 16 hr light/8 hr dark cycle, and a light intensity of 100 μE/sec/m$^2$, for three weeks on PM medium containing 4.4 g MS salts (Sigma Chemical Co., St. Louis, Mo.), 30 g sucrose, 0.17 g NaH$_2$PO$_4$.H$_2$O, 0.4 mg thiamine-HCl, 25 g ascorbic acid, and 0.1 g inositol per liter, pH 6.0, and 0.2% Gelrite agar. The stems were cut into 3–5 mm segments.

Before inoculation, 30 stem segments were placed onto a co-culture plate to serve as noninoculated controls. Co-culture plates contained 0.9% agar-solidified 1/10 MS salts (Murashige et al. (1962) *Physiol. Plant.* 15:473) and 3% sucrose, and were prepared by first coating the agar with 2 mls of 6–7 day old tobacco suspension cells as a feeder layer (Fraley et al. (1983) *Proc. Natl. Acad. Sci. USA* 80:4803), and then overlaying these cells with an 8.5 cm disc of sterile Whatman filter paper.

The explant segments to be transformed were inoculated by pouring the diluted bacterial suspension onto the stem pieces and allowing the mixture to incubate for 15 min. The bacterial suspension was then aspirated off the explant segments, which were subsequently spread evenly onto co-culture plates (about 90 stem pieces per plate). After a 2 day co-culture period at 19° C. under a 16 hr light/8 hr dark cycle and a light intensity of 100 μE/sec/m$^2$, the explants were placed onto 0.9% agar-solidified callus induction medium containing 1X MS salts, 5.0 mg/l zeatin riboside, 10 mg/l AgNO$_3$, 3% sucrose, 500 mg/l carbenicillin, and 0.1 mg/l napththaleneacetic acid, and incubated at 19° C. under a 16 hr light/8 hr dark cycle for 2 days. Explants were subsequently transferred onto callus induction medium supplemented with 0.025 mM glyphosate for selection. After 4 weeks, explants were placed onto 0.9% agar-solidified shoot induction medium containing 1X MS salts, 5.0 mg/A zeatin riboside, 10 mg/l AgNO$_3$, 3% sucrose, 500 mg/l carbenicillin, 0.3 mg/l GA3, and 0.025 mM glyphosate. Shoots began to appear at 8 weeks. Explants were transferred to fresh shoot induction medium every 4 weeks over a 12 week period. Shoots were excised from calli and placed on PM medium solidified with 0.2% Gelrite agar for about 2 weeks or until they developed roots and were large enough to be placed into soil. Once transplanted into Metro-Mix 350 (Hummert Seed Co., St. Louis), seedlings were grown in the greenhouse for 2–3 months under a 14 hr light/8 hr dark regime under a light intensity of 600–700 μEn/sec/m$^2$, a day temperature of 65°–75° F., a night temperature of 55°–65° F., and a relative humidity of 60%.

Analysis of Antifumgal Polypeptide Expression in transgenic Potato Plants

Leaf samples (20 to 100 mg) were taken from transgenic plants grown to 1 to 2 inches in height. The leaf samples were ground in PBST buffer (15 μl/mg tissue) containing 1 mM KH$_2$PO$_4$, 10 mM Na$_2$HPO$_4$, 137 mM NaCl, 2.7 mM KCl, pH 7.4, and 0.05% Tween-20, and allowed to sit at 4° C. overnight. After centrifugation, 100 μl of the supernatant were used in an ELISA assay. Polyclonal antibodies against Rs-AFP1 polypeptide (SEQ ID NO:18) were prepared by Pocono Rabbit Farm (Pocono, Pa.). Wells of a Nunc Maxisorp 96 well plate (Nunc #4-39454) were coated with antibodies against Rs-AFP1 polypeptide by adding 100 μl of antibodies (1 mg IgG/ml) diluted 1:200 in coating buffer containing 1.59 g Na$_2$CO$_3$ and 2.93 g NaHCO$_3$ per liter distilled water, pH 9.6, and incubating at 4° C. overnight. The coating solution was then removed from the wells, which were then washed three times with PBST. One hundred μl of leaf supernatant or appropriately diluted polypeptide standards in PBST supplemented with 0.2% (w/v) BSA, fraction V (Sigma, St. Louis) were added to the wells. The concentration of each polypeptide in extracts from transgenic plants was determined from standard curves constructed using varying amounts of the respective purified polypeptide. AlyAFP, Rs-AFP1, and Rs-AFP2 cross-reacted with the polyclonal antibody preparation. After overnight incubation at 4° C., the solutions were removed from the wells, and the wells were washed three times with PBST. One hundred μl of a 1:1000 dilution in PBST of a 0.5 mg/ml Rs-AFP1 antibody/alkaline phosphatase conjugate prepared according to Boorsma et al. ((1975) *J. Histochem. Cytochem.* 23: 200–207) were added to each well. The plate was incubated at 22° C. for 4 hours, and the wells were then washed five times with PBST. One hundred μl of a freshly prepared solution of p-nitrophenyl phosphate (1 mg/ml) (Sigma Chemical Co., St. Louis, Mo.) dissolved in 200 mM Tris buffer, pH 9, were added to each well, and the plate was incubated at 22° C. for 1 hour. The optical density at 405 nm was determined using a Thermo-max microplate reader (Molecular Devices, Menlo Park, Calif.). Plants expressing different levels of antifungal polypeptides were used for susbsequent disease tests.

Verticillium Wilt Control in Transgenic Plants

Conidia and mycelia of a 2–3 week old culture of virulent *Verticillium dahliae* were used to inoculate a PDA (potatoes, 200 g/l; Bacto dextrose, 20 g/l; and Bacto agar, 15 g/l) Petri plate. This culture was allowed to grow at 22° C. for 4–5 days. Conidia were then harvested by washing the culture plate with sterile distilled water and filtering the liquid through two layers of cheesecloth. The conidial spore concentration was determined using a hemacytometer, and adjusted to 1×10$^6$ conidia/ml with sterile distilled water.

Transgenic and non-transgenic potato plants were grown from stem cuttings under sterile conditions as described above in plastic cups containing 50 mls of PM-agar medium.

When plants were about 1–2 inches tall, they were removed from the medium and their roots were dipped in the spore suspension (Joaquim et al. (1991) *Phytopathology* 81:552–558). The inoculated plants were then transplanted into 6-inch pots containing Metro-Mix 350. After transplanting, each plant received an additional 5 mls of the spore suspension on the soil surface around the base of the stem. The pots were placed in a growth chamber under the following conditions: temperature at 20° C., light intensity at 320 μEinstein/sec/cm$^{2}$, 12 hr day/12 hr night light cycle, subirrigation with water 2 times/day, 20 minutes soaking each time. Four weeks after inoculation, the plants were scored for disease severity on a scale of 0–100% (Horsfall et al. (1945) *Phytopathology* 35:655). To develop a disease progress curve over time, plants were rated once a week for at least 8 weeks.

RESULTS

Verticillium Wilt Resistance in AlyAfp-Expressing Potato Plants

Figure 7:
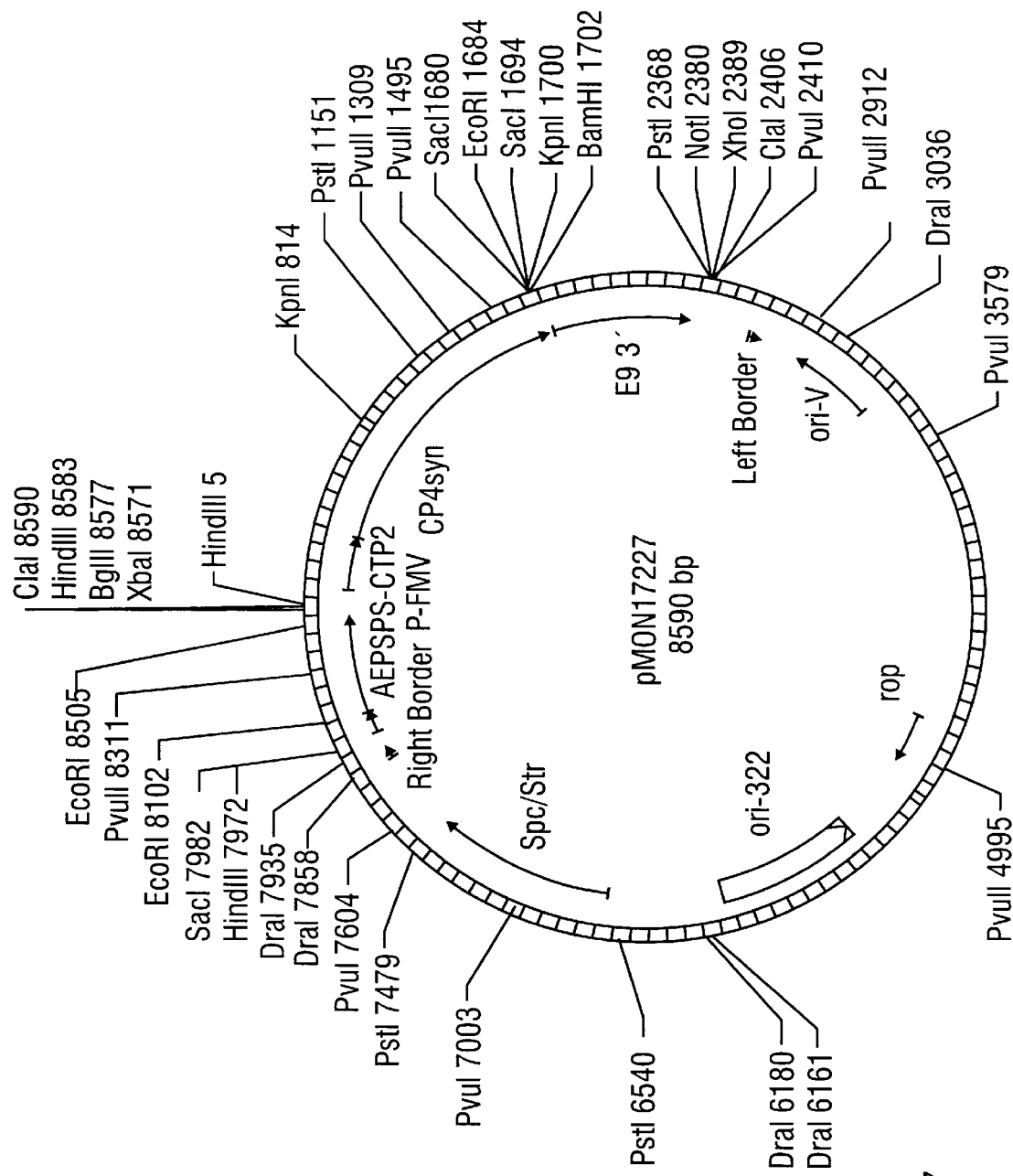
FIG. 7 is a physical map of pMON17227.
Figure 8:
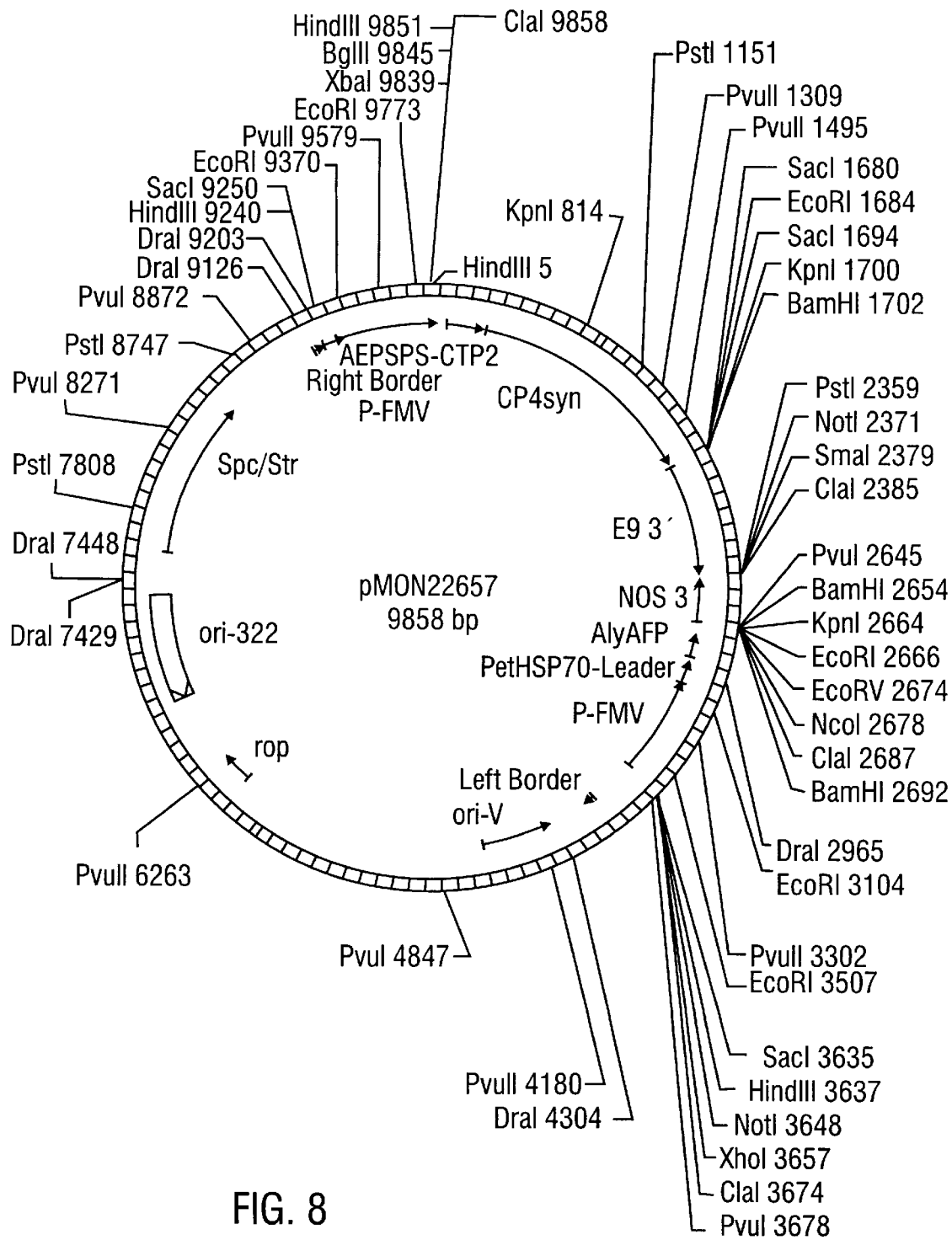
FIG. 8 is a physical map of pMON22657.

Ten independent transgenic potato lines expressing AlyAFP were tested for resistance to Verticillium wilt disease. Among these lines, 5 were high expressers of AlyAFP, containing from 5.2 to 14.9 μg AlyAFP/g fresh leaf tissue; 3 were medium expressers, containing 2.6 μg AlyAFP/g fresh leaf tissue; and 2 were low expressers, containing from 0.9 to 1.1 μg/g fresh leaf tissue (Table 3). The expression level in leaves is an indicator of the expression in the whole plant since the FMV promoter used to drive expression of the respective encoding DNAs directs gene expression constitutively in all tissue types of potato plants. In the test, 3 independent transgenic lines were also included as negative controls. These were generated from transformations employing Agrobacterium harboring plasmid pMON17227 (vector control; FIG. 7), which does not contain any antifungal polypeptide-encoding DNA. Other controls included in the test were nontransgenic potato Russet Burbank, which was used as the host for the transformation experiments; nontransgenic potato variety Russet Ranger, which is more resistant to Verticillium wilt than Russet Burbank; and non-transgenic potato variety Norchip, which is more susceptible to Verticillium wilt than Russet Burbank.

Table 3 summarizes the protein expression level in each of the lines, and the disease severity rating of each individual line in the test determined at 44 days post inoculation. The disease severity rating was the average of 3 replicates. For convenience, the same disease data are also presented as a bar graph in FIG. 11. The order of appearance of each potato line in Table 3 (from top to bottom) and in FIG. 11 (from left to right) is the same.

TABLE 3

Expression of AlyAFP and Verticillium Wilt Resistance in Transgenic Potato Plants

| Plants | Line# | Protein Expression (μg AFP/g tissue) | Disease Severity (%) (44 Days Post Inoc.) | Average Dis. Sev. |
|---|---|---|---|---|
| AlyAFP plants | 17575 | 14.9 | 7.5 | + |
| | 17578 | 12.7 | 15 | + |
| | 17581 | 9.2 | 24.3 | + |
| | 17587 | 9.6 | 6.3 | + |
| | 17595 | 5.2 | 21 | + |
| | 17618 | 2.6 | 16.3 | + |
| | 17593 | 2.6 | 17.3 | + |
| | 17592 | 2.6 | 11.8 | + |
| | 17589 | 1.1 | 43.8 | |
| | 17580 | 0.9 | 33.3 | |
| | | | | 14.9 |
| Vector control | 17227-1 | 0 | 31.3 | + |
| | 17227-2 | 0 | 45 | + |
| | 17227-5 | 0 | 41.3 | + |
| | | | | 39.2 |
| Non-transgenic Russet Burbank | | 0 | 16.7 | |
| Non-transgenic Russet Ranger | | 0 | 13.3 | |
| Non-transgenic Norchip | | 0 | 75 | |

Figure 11:
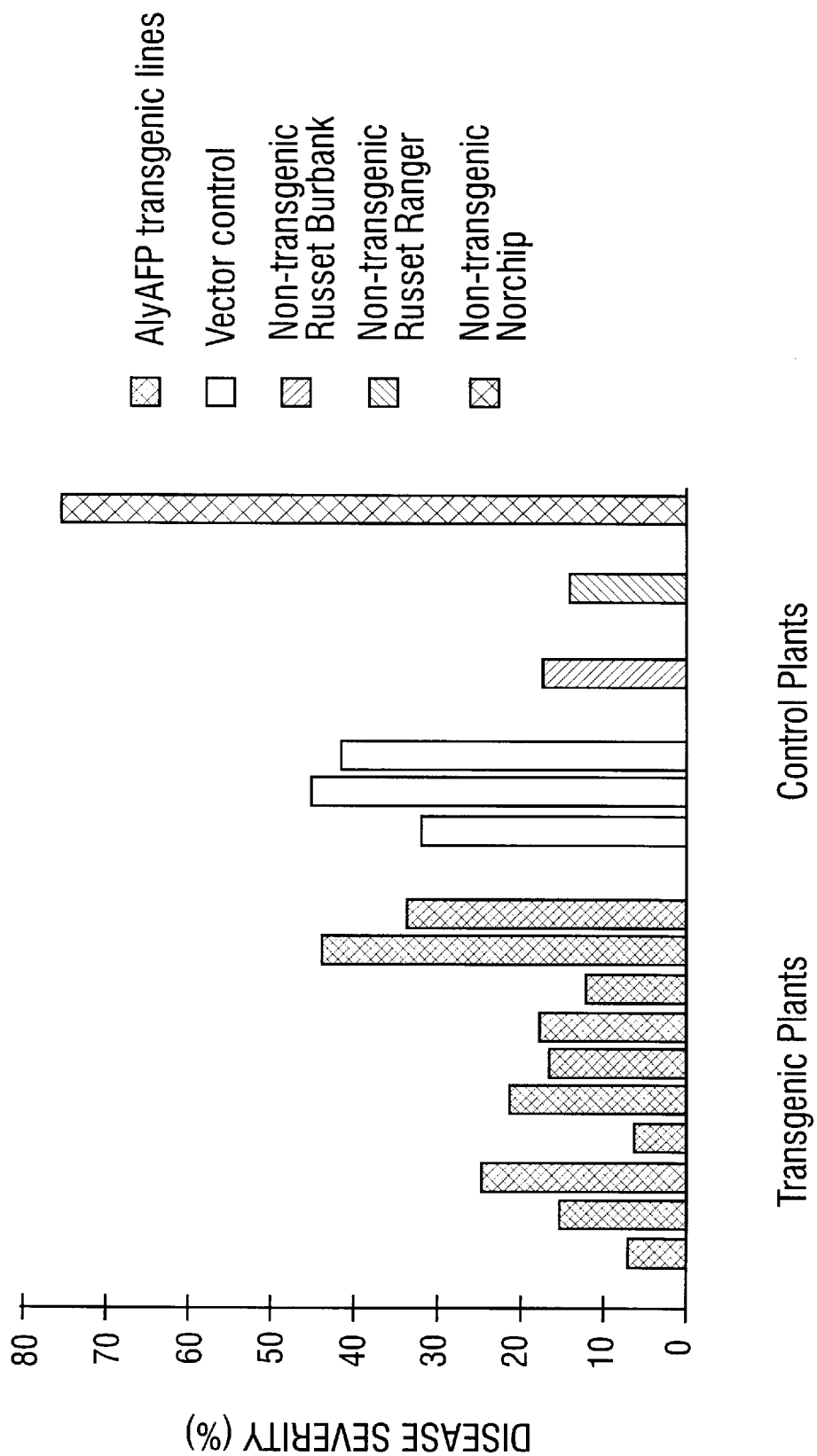
FIG. 11 is a bar graph, corresponding to the data in Table 3, showing the results of a Verticillium wilt disease test conducted on transgenic potato plants expressing AlyAFP cDNA.

As shown in Table 3 and FIG. 11, disease severity on the high and medium AlyAFP expressing plants averaged 62% less than that of the vector control. This was calculated as follows: [(average of 3 vector control lines) - (average of 8 lines of high and medium expressors)]×100% / (average of 3 vector control lines). The best high expressing lines, such as line #17575 and line #17587, exhibited disease severities that were 82% less than that of the vector control. The low expressing lines did not exhibit any significant level of disease resistance as compared to the vector controls. In Table 3, "+" denotes lines that were included in the foregoing calculation of the average disease severity.

These results demonstrate that potato plants expressing AlyAFP at and above 2.6 μg/g fresh leaf tissue exhibit resistance to Verticillium wilt. The level of disease resistance correlates to the AlyAFP expression level. These results also demonstrate that the expression level of AlyAFP required for significant disease resistance is close to the IC$_{50}$ value determined in the in vitro antifungal assays presented in Example 3. Although the non-transgenic Russet Burbank plants exhibited a relatively low disease severity rating, the plants were severely stunted compared to Russet Ranger plants. This stunting phenotype was not accounted for in the disease severity rating.

Verticillium Wilt Resistance in Rs-AFP1-and Rs-AFP2-Expressin Potato Plants

Transgenic potato lines expressing Rs-AFP1 and Rs-AFP2 were tested for Verticillium wilt disease resistance in an experiment similar to that described above for AlyAFP-expressing plants. Five independent lines of Rs-AFP1 expressing plants containing from 5.2 to 26 μg Rs-AFP1/g fresh leaf tissue, and 5 independent lines of Rs-AFP2 expressing plants containing from 10.8 to 25.2 μg Rs-AFP2/g fresh leaf tissue, were tested in this experiment, the results of which are shown in Table 4. The same controls as those used above in the case of AlyAFP-expressing plants were employed in these experiments.

In this test, disease symptoms appeared in the experimental and control plants at approximately 49 days post inoculation. Disease progress was rated at 49, 58, and 64 days post inoculation. No differences were observed between Rs-AFP1-and Rs-AFP2-expressing lines and the control lines at any of these timepoints. The disease severity rating was the average of three replicates. Table 4 summarizes the protein expression level in each of the lines, and the disease severity rating of each individual line determined at 58 days post inoculation. For convenience, the same disease data are also presented as a bar graph in FIG. 12. The order of appearance of each potato line in Table 4 (from top to bottom) and in FIG. 12 (from left to right) is the same.

TABLE 4

Expression of Rs-AFP1 and Rs-AFP2 and
Verticillium Wilt Resistance in Transgenic Potato Plants

| Plants | Line# | Protein Expression (μg AFP/g tissue) | Disease Severity (%) (58 Days Post Inoc.) | Average Dis. Sev. |
|---|---|---|---|---|
| Rs-AFP1 plants | 15124 | 26 | 56.3 | + |
| | 15143 | 18.3 | 78.8 | + |
| | 15117 | 9.7 | 47.5 | + |
| | 15120 | 8.0 | 50.0 | + |
| | 15154 | 5.2 | 66.3 | + |
| | | | | 59.8 |
| Rs-AFP2 plants | 13501 | 25.2 | 76.3 | + |
| | 13503 | 25.1 | 53.8 | + |
| | 13532 | 17.5 | 35.0 | + |
| | 13531 | 16.2 | 72.5 | + |
| | 13500 | 10.8 | 82.5 | + |
| | | | | 64.0 |
| Vector control | 17227-1 | 0 | 56.3 | + |
| | 17227-5 | 0 | 63.8 | + |
| | | | | 60.0 |
| Non-transgenic Russet Burbank | | 0 | 85 | |
| Non-transgenic Russet Ranger | | 0 | 16.3 | |

TABLE 4-continued

Expression of Rs-AFP1 and Rs-AFP2 and
Verticillium Wilt Resistance in Transgenic Potato Plants

| Plants | Line# | Protein Expression (μg AFP/g tissue) | Disease Severity (%) (58 Days Post Inoc.) | Average Dis. Sev. |
|---|---|---|---|---|
| Non-transgenic Norchip | | 0 | 82.5 | |

Figure 12:
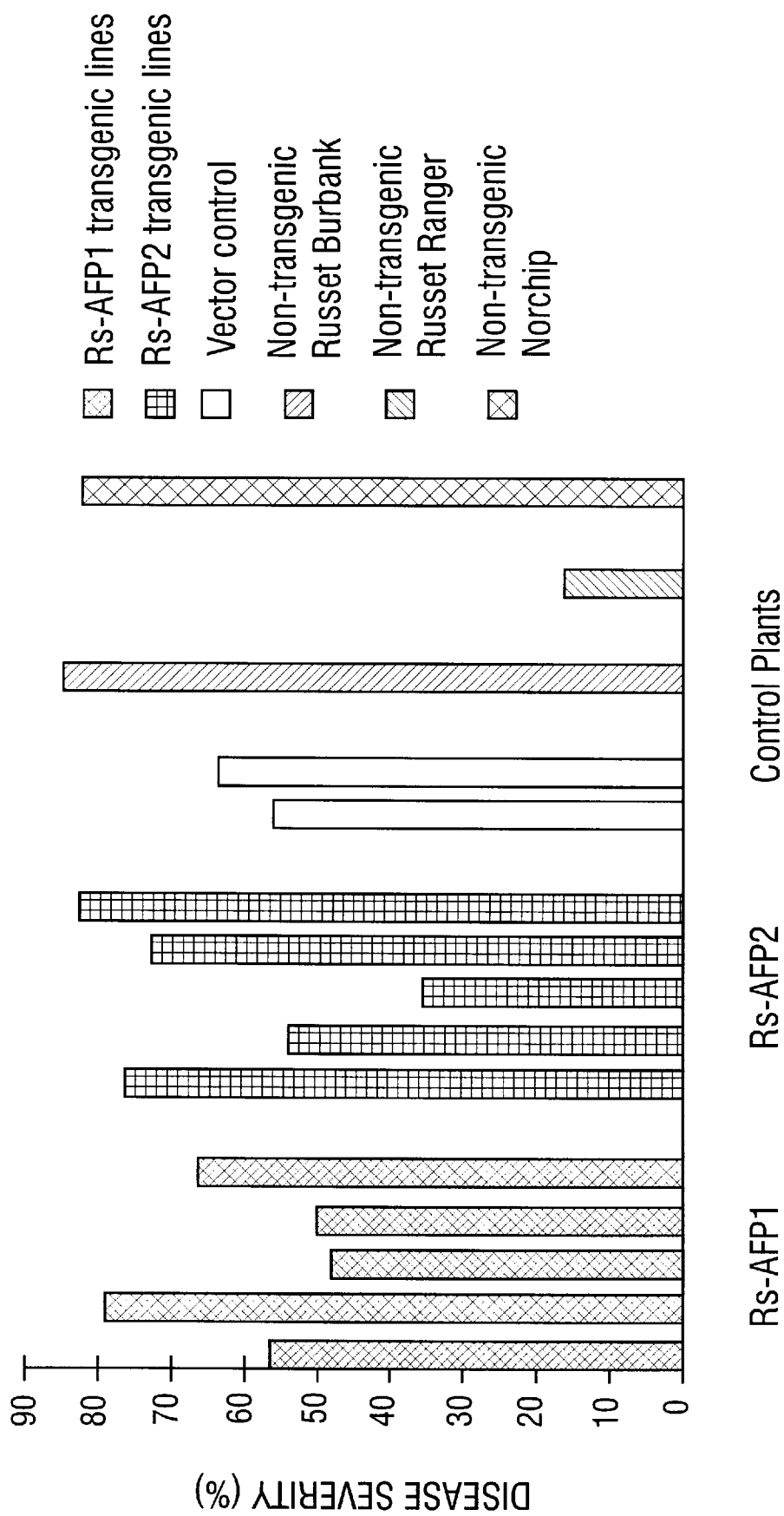
FIG. 12 is a bar graph, corresponding to the data in Table 4, showing the results of a Verticillium wilt disease test conducted on transgenic potato plants expressing Rs-AFP1 and Rs-AFP2 synthetic DNAs.

As shown in Table 4 and FIG. 12, the average disease severities on the high expressing Rs-AFP1 and Rs-AFP2 plants were 59.8% and 64.0%, respectively. This was essentially the same as that of the vector control (60.0%). In Table 4, "+" denotes lines that were included in the calculation of the average disease severity.

In summary, the disease test results obtained with transgenic plants expressing AlyAFP, Rs-AFP1, and Rs-AFP2 demonstrate that AlyAFP confers Verticillium wilt resistance to potato plants at an expression level as low as 2.6 μg/g fresh leaf tissue, whereas Rs-AFP1 and Rs-AFP2 did not provide any significant level of Verticillium wilt resistance to potato plants even at expression levels as high as 25 μg/g fresh leaf tissue. These results indicate that the $IC_{50}$ values for AlyAFP determined in Example 3 are a reliable indicator of the usefulness of this protein in controlling damage caused by undesired fungi, and in genetically engineering disease resistance in plants.

The invention being thus described, it is obvious that the same can be varied in many ways. Such variations are not to be regarded as a departure from the spirit and scope of the present invention, and all such modifications as would be obvious to one skilled in the art are intended to be included within the scope of the following claims.

What is claimed is:

1. A purified nucleic acid segment encoding an antifungal protein having the sequence of SEQ ID NO:2.

2. The purified nucleic acid segment of claim 1 further defined as comprising the nucleic acid sequence of SEQ ID NO:12 or the complement thereof.

3. The purified nucleic acid segment of claim 1, further defined as an RNA segment.

4. The nucleic acid segment of claim 1, comprising nucleotides 116 to 269 of the nucleotide sequence shown in SEQ ID NO:12.

5. A recombinant, double-stranded DNA molecule, comprising the following sequences operatively linked in the 5' to 3' direction:

a) a promoter that functions in plant cells to cause transcription of an adjacent coding sequence;

b) a coding sequence that encodes a protein comprising an antifungal protein having the sequence of SEQ ID NO:2; and c) a 3' non-translated sequence that functions in plant cells to cause transcriptional termination and the addition of polyadenylate nucleotides to the 3' end of the transcribed RNA sequence.

6. The DNA molecule of claim 5, wherein said coding sequence is a CDNA molecule.

7. The DNA molecule of claim 6, wherein said CDNA is selected from the group consisting of the nucleotide sequence shown in SEQ ID NO:12, and nucleotides 116 to 269 of the nucleotide sequence shown in SEQ ID NO:12.

8. The DNA molecule of Claim 5, wherein said promoter is selected from the group consisting of the FMV 35S promoter, the CaMV 35S promoter, the ssRUBISCO promoter, the EIF-4A promoter, the LTP promoter, the actin promoter, and the ubiquitin promoter.

9. A method of controlling fungal damage to a plant, comprising the steps of:

a) inserting into the genome of plant cells a recombinant, double-stranded DNA molecule comprising the following sequences operatively linked in the 5' to 3' direction:

(i) a promoter sequence that functions in plant cells to cause the transcription of an adjacent coding sequence;

(ii) a coding sequence that encodes a polypeptide having the amino acid sequence of SEQ ID NO:2; and (iii) a 3' non-translated sequence that functions in plant cells to cause transcriptional termination and the addition of polyadenylation nucleotides to the 3' end of the transcribed RNA sequence;

b) obtaining transformed plant cells; and c) regenerating from said transformed plant cells a genetically transformed plant, cells of which express an antifungal effective amount of the polypeptide.

10. The method of claim 9, wherein said coding sequence is selected from the group consisting of the nucleotide sequence shown in SEQ ID NO:12, and nucleotides 116 to 269 of the nucleotide sequence shown in SEQ ID NO:12.

11. The method of claim 9, wherein said promoter is selected from the group consisting of the FMV 35S promoter, the CaMV 35S promoter, the ssRUBISCO promoter, the EIF-4A promoter, the LTP promoter, the actin promoter, and the ubiquitin promoter.

12. A transonic plant, cells of which contain an antifungal effective amount of a polypeptide comprising an antifungal protein having the amino acid sequence of SE ID NO:2.

13. The transonic plant of claim 12, wherein said plant is produced by a method comprising the steps of:

a) inserting into the genome of plant cells a recombinant, double-stranded DNA molecule comprising:

(i) a promoter sequence that functions in plant cells to cause the transcription of an adjacent coding sequence;

(ii) a coding sequence that encodes a polypeptide comprising the amino acid sequence shown in SEQ ID NO:2;

(iii) a 3' non-translated sequence that functions in plant cells to cause transcriptional termination and the addition of polyadenylate nucleotides to the 3' end of the transcribed RNA sequence;

b) obtaining transformed plant cells; and c) regenerating from said transformed plant cells a genetically transformed plant, cells of which express an antifungal effective amount of the polypeptide.

14. The plant of claim 13, wherein said coding sequence is selected from the group consisting of the nucleotide sequence shown in SE ID NO:12, and nucleotides 116 to 269 of the nucleotide sequence shown in SE ID NO:12.

15. The plant of claim 12, the genome of which further comprises DNA encoding a *B.t.* endotoxin, wherein said DNA is expressed and produces an anti-insect effective amount of said *B.t.* endotoxin.

16. The plant of claim 12, wherein said plant is selected from the group consisting of apple, barley, broccoli, cabbage, canola, carrot, citrus, corn, cotton, garlic, oat, onion, an ornamental plant, pea, peanut, pepper, potato, rice, rye, sorghum, soybean, strawberry, sugarbeet, sugarcane, tomato, a vine, and wheat.

17. The plant of claim 12, wherein said plant is a potato plant.

18. Seeds produced by said plant of claim 17.

19. Progeny of the claim 12.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 49 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:1:

Arg Leu Cys Glu Arg Pro Ser Gly Thr Xaa Ser Gly Val Cys Gly Asn
1               5                   1 0                  1 5

Asn Asn Ala Cys Arg Asn Gln Cys Arg Asn Leu Glu Arg Ala Glu His
            2 0                  2 5                  3 0

Gly Ser Cys Asn Tyr Val Phe Pro Ala His Lys Xaa Xaa Xaa Tyr Phe
            3 5                  4 0                  4 5

Pro ( 2 ) INFORMATION FOR SEQ ID NO:2:

( i ) SEQUENCE CHARACTERISTICS:
( A ) LENGTH: 50 amino acids
( B ) TYPE: amino acid (C) STRANDEDNESS:
(D) TOPOLOGY: linear (ii) MOLECULE TYPE: peptide (xi) SEQUENCE DESCRIPTION: SEQ ID NO:2:

Arg Leu Cys Glu Arg Pro Ser Gly Thr Trp Ser Gly Val Cys Gly Asn
1               5                   10                  15

Asn Asn Ala Cys Arg Asn Gln Cys Arg Asn Leu Glu Arg Ala Glu His
            20              25                      30

Gly Ser Cys Asn Tyr Val Phe Pro Ala His Lys Cys Ile Cys Tyr Phe
        35                  40              45

Pro Cys
    50

(2) INFORMATION FOR SEQ ID NO:3:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(ix) FEATURE:
(A) NAME/KEY: modified_base
(B) LOCATION: 18
(D) OTHER INFORMATION: /mod_base=i (ix) FEATURE:
(A) NAME/KEY: modified_base
(B) LOCATION: 21
(D) OTHER INFORMATION: /mod_base=i (xi) SEQUENCE DESCRIPTION: SEQ ID NO:3:

GGGAATTCGG ATCCACANGG NAARTARCAD ATRCA       35

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(ix) FEATURE:
(A) NAME/KEY: modified_base
(B) LOCATION: 18
(D) OTHER INFORMATION: /mod_base=i (ix) FEATURE:
(A) NAME/KEY: modified_base
(B) LOCATION: 19
(D) OTHER INFORMATION: /mod_base=i (ix) FEATURE:
(A) NAME/KEY: modified_base
(B) LOCATION: 23
(D) OTHER INFORMATION: /mod_base=i (ix) FEATURE:
(A) NAME/KEY: modified_base
(B) LOCATION: 24
(D) OTHER INFORMATION: /mod_base=i (ix) FEATURE:
(A) NAME/KEY: modified_base
(B) LOCATION: 28

(D) OTHER INFORMATION: /mod_base=i (ix) FEATURE:
    (A) NAME/KEY: modified_base
    (B) LOCATION: 29
    (D) OTHER INFORMATION: /mod_base=i (xi) SEQUENCE DESCRIPTION: SEQ ID NO:4:

GGGAATTCGG ATCCGGGNNG GGNNGGGNNG     30

(2) INFORMATION FOR SEQ ID NO:5:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGGGGGGGGG GGGGGGCACA CNTCCCTAC ACATAGATAT ACATACAAAA TCACAGAAAG     60

TAATAGATAT GGCTAAGTGT GCTTCCATCA TCTCCTTGT CTCTGCTGCT CTTGTTCTCT     120

TTGCTGCTTT TGAAGCACCA GCAATGGTGG AGTCACGGAA GTTGTGCGAG AGTCCAAGTG     180

GAACATGGTC AGGCGTGTGT GGAAACAACA ATGCTTGCAA GAATCAGTGC ATTAACCTTG     240

AAGGAGCNCG ACATGGATCT TGCAACTATG TCTTCCCAGC TCACAAGTGC ATATGCTACT     300

TCCCCTGT     308

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: modified_base
        (B) LOCATION: 17
        (D) OTHER INFORMATION: /mod_base=i (ix) FEATURE:
        (A) NAME/KEY: modified_base
        (B) LOCATION: 23
        (D) OTHER INFORMATION: /mod_base=i (xi) SEQUENCE DESCRIPTION: SEQ ID NO:6:

GGGAATTCGG ATCCGTNTGY GGNAAYAAYA AYGC     34

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:7:

GGGAATTCGG ATCCTTTTTT TTTTTTTTTT TT     32

(2) INFORMATION FOR SEQ ID NO:8:

( i ) SEQUENCE CHARACTERISTICS:
 ( A ) LENGTH: 306 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:8:

| | | | | | | |
|---|---|---|---|---|---|---|
| GTGTGTGGGA | ATAATAACGC | ATGCAGGAAC | CAATGCAGAA | ACCTTGAAAG | AGCAGAACAC | 60 |
| GGATCTTGCA | ACTATGTCTT | CCCAGCTCAC | AAATGTATTT | GTTACTTCCC | ATGTTAATCT | 120 |
| ACCAAATCAC | TTTTTGTGCT | TGTGTGTGTA | TTTTACATGT | TATGTGTTTA | TTTACATGAA | 180 |
| ATAAGTCTGT | GTCATCCTTA | TGGGTGACCT | TATGACATGT | ACCAGATATA | TCATATATGT | 240 |
| ATGTTGGTTT | GTTGTGTGGC | AATTATAAAC | TTTTATTTGT | GGATGCAAAA | AAAAAAAAA | 300 |
| AAAAAA | | | | | | 306 |

( 2 ) INFORMATION FOR SEQ ID NO:9:

( i ) SEQUENCE CHARACTERISTICS:
 ( A ) LENGTH: 500 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:9:

| | | | | | | |
|---|---|---|---|---|---|---|
| GGGGGGGGGG | GGGGGGCACA | CNTCCCTAC | ACATAGATAT | ACATACAAAA | TCACAGAAAG | 60 |
| TAATAGATAT | GGCTAAGTGT | GCTTCCATCA | TCTCCCTTGT | CTCTGCTGCT | CTTGTTCTCT | 120 |
| TTGCTGCTTT | TGAAGCACCA | GCAATGGTGG | AGTCACGGAA | GTTGTGCGAG | AGTCCAAGTG | 180 |
| GAACATGGTC | AGGCGTGTGT | GGGAATAATA | ACGCATGCAG | GAACCAATGC | AGAAACCTTG | 240 |
| AAAGAGCAGA | ACACGGATCT | TGCAACTATG | TCTTCCCAGC | TCACAAATGT | ATTTGTTACT | 300 |
| TCCCATGTTA | ATCTACCAAA | TCACTTTTTG | TGCTTGTGTG | TGTATTTAC | ATGTTATGTG | 360 |
| TTTATTTACA | TGAAATAAGT | CTGTGTCATC | CTTATGGGTG | ACCTTATGAC | ATGTACCAGA | 420 |
| TATATCATAT | ATGTATGTTG | GTTTGTTGTG | TGGCAATTAT | AAACTTTTAT | TTGTGGATGC | 480 |
| AAAAAAAAAA | AAAAAAAAA | | | | | 500 |

( 2 ) INFORMATION FOR SEQ ID NO:10:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "synthetic DNA"

( x i ) SEQUENCE DESCRIPTION: SEQ ID NO:10:

| | | | |
|---|---|---|---|
| GGGAATTCGG | ATCCAASAAA | GTAATAGWTA | TGGCTAAG | 38 |

( 2 ) INFORMATION FOR SEQ ID NO:11:

( i ) SEQUENCE CHARACTERISTICS:
 ( A ) LENGTH: 40 base pairs
 ( B ) TYPE: nucleic acid
 ( C ) STRANDEDNESS: single
 ( D ) TOPOLOGY: linear ( i i ) MOLECULE TYPE: other nucleic acid (A) DESCRIPTION: /desc = "synthetic DNA"

(x i) SEQUENCE DESCRIPTION: SEQ ID NO:11:

GGGAATTCGG ATCCTTATTA ACATGGGAAG TAACAAATAC                    40

(2) INFORMATION FOR SEQ ID NO:12:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:12:

GGGAATTCGG ATCCAAGAAA GTAATAGATA TGGCTAAGTT TGCTACCATC ATCTCTCTTC      60
TCTTTGCTGC TCTTGTTCTC TTTGCTGCCT TGAAGCACC AACAATGGTG GATGCAAGGT    120
TGTGCGAGAG ACCAAGTGGG ACATGGTCAG GAGTTTGTGG GAACAACAAT GCATGCAGGA    180
ACCAATGCAG AAACCTTGAA AGAGCAGAAC ACGGATCTTG CAACTATGTC TTCCCAGCTC    240
ACAAATGTAT TTGTTACTTC CCATGTTAAT AAGGATCCGA ATTCCC                    286

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "synthetic DNA"

(x i) SEQUENCE DESCRIPTION: SEQ ID NO:13:

CTAGTGTTGA CCAGTGTTAC TC                                              22

(2) INFORMATION FOR SEQ ID NO:14:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:14:

GGATCCAASA AAGTAATAGW TATGGCTAAG TTTGCTACCA TCATCTCTCT TCTCTTTGCT      60
GCTCTTGTTC TCTTTGCTGC CTTTGAAGCA CCAACAATGG TGGATGCAAG GTTGTGCGAG    120
AGACCAAGTG GGACATGGTC AGGAGTTTGT GGGAACAACA ATGCATGCAG GAACCAATGC    180
AGAAACCTTG AAAGAGCAGA ACACGGATCT TGCAACTATG TCTTCCCAGC TCACAAATGT    240
ATTTGTTACT TCCCATGTTA ATAAGGATCC                                      270

(2) INFORMATION FOR SEQ ID NO:15:

(i) SEQUENCE CHARACTERISTICS:
        (A) LENGTH: 79 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:15:

| | | | | | | | | | | | | | | |
|---|---|---|---|---|---|---|---|---|---|---|---|---|---|---|
| Met | Ala | Lys | Phe | Ala | Thr | Ile | Ile | Ser | Leu | Leu | Phe | Ala | Ala | Leu | Val |
| 1 | | | | 5 | | | | | 10 | | | | | 15 |
| Leu | Phe | Ala | Ala | Phe | Glu | Ala | Pro | Thr | Met | Val | Asp | Ala | Arg | Leu | Cys |
| | | | 20 | | | | | 25 | | | | | 30 | | |
| Glu | Arg | Pro | Ser | Gly | Thr | Trp | Ser | Gly | Val | Cys | Gly | Asn | Asn | Asn | Ala |
| | | 35 | | | | | 40 | | | | | | 45 | | |
| Cys | Arg | Asn | Gln | Cys | Arg | Asn | Leu | Glu | Arg | Ala | Glu | His | Gly | Ser | Cys |
| | 50 | | | | | 55 | | | | | 60 | | | | |
| Asn | Tyr | Val | Phe | Pro | Ala | His | Lys | Cys | Ile | Cys | Tyr | Phe | Pro | Cys | |
| 65 | | | | | 70 | | | | 75 | | | | | | |

(2) INFORMATION FOR SEQ ID NO:16:

(i) SEQUENCE CHARACTERISTICS:
    (A) LENGTH: 285 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA"

(xi) SEQUENCE DESCRIPTION: SEQ ID NO:16:

| | | | | | |
|---|---|---|---|---|---|
| TCCGGATCCT | CTAGAGTTTT | ATTAGTGATC | ATGGCTAAGT | TTGCGTCCAT | CATCGCACTC | 60 |
| CTCTTTGCTG | CTCTCGTTCT | CTTTGCTGCT | TTCGAGGCAC | CAACTATGGT | GGAGGCACAA | 120 |
| AAGTTGTGCG | AGAGGCCATC | AGGGACTTGG | TCAGGAGTCT | GCGGAAACAA | CAACGCATGC | 180 |
| AAGAACCAAT | GCATCAACCT | CGAGAAGGCA | CGGCATGGAT | CTTGCAACTA | CGTCTTCCCA | 240 |
| GCTCACAAGT | GCATCTGCTA | CTTTCCATGC | TAATAGGAAT | TCGAA | | 285 |

(2) INFORMATION FOR SEQ ID NO:17:

(i) SEQUENCE CHARACTERISTICS:
    (A) LENGTH: 285 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA"

(xi) SEQUENCE DESCRIPTION: SEQ ID NO:17:

| | | | | | |
|---|---|---|---|---|---|
| TCCGGATCCT | CTAGAGTTTT | ATTAGTGATC | ATGGCTAAGT | TTGCGTCCAT | CATCGCACTC | 60 |
| CTCTTTGCTG | CTCTCGTTCT | CTTTGCTGCT | TTCGAGGCAC | CAACTATGGT | GGAGGCACAA | 120 |
| AAGTTGTGCC | AAAGGCCATC | AGGGACTTGG | TCAGGAGTCT | GCGGAAACAA | CAACGCATGC | 180 |
| AAGAACCAAT | GCATCAGACT | CGAGAAGGCA | CGGCATGGAT | CTTGCAACTA | CGTCTTCCCA | 240 |
| GCTCACAAGT | GCATCTGCTA | CTTTCCATGC | TAATAGGAAT | TCGAA | | 285 |

(2) INFORMATION FOR SEQ ID NO:18:

(i) SEQUENCE CHARACTERISTICS:
    (A) LENGTH: 51 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:18:

| | | | | | | | | | | | | | | | |
|---|---|---|---|---|---|---|---|---|---|---|---|---|---|---|---|
| Gln | Lys | Leu | Cys | Glu | Arg | Pro | Ser | Gly | Thr | Trp | Ser | Gly | Val | Cys | Gly |
| 1 | | | | 5 | | | | | 10 | | | | | 15 | |

```
Asn  Asn  Asn  Ala  Cys  Lys  Asn  Gln  Cys  Ile  Asn  Leu  Glu  Lys  Ala  Arg
               20                  25                       30

His  Gly  Ser  Cys  Asn  Tyr  Val  Phe  Pro  Ala  His  Lys  Cys  Ile  Cys  Tyr
          35                       40                       45

Phe  Pro  Cys
     50
```

( 2 ) INFORMATION FOR SEQ ID NO:19:

( i ) SEQUENCE CHARACTERISTICS:
      ( A ) LENGTH: 51 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:19:

```
Gln  Lys  Leu  Cys  Gln  Arg  Pro  Ser  Gly  Thr  Trp  Ser  Gly  Val  Cys  Gly
1                   5                   10                      15

Asn  Asn  Asn  Ala  Cys  Lys  Asn  Gln  Cys  Ile  Arg  Leu  Glu  Lys  Ala  Arg
               20                  25                       30

His  Gly  Ser  Cys  Asn  Tyr  Val  Phe  Pro  Ala  His  Lys  Cys  Ile  Cys  Tyr
          35                       40                       45

Phe  Pro  Cys
     50
```